US012807552B2

(12) United States Patent
Kothandaraman et al.

(10) Patent No.: US 12,807,552 B2
(45) Date of Patent: Nov. 24, 2026

(54) COMBINED CAPTURE AND CONVERSION OF CO2 TO METHANOL IN A POST COMBUSTION CAPTURE SOLVENT

(71) Applicant: BATTELLE MEMORIAL INSTITUTE, Richland, WA (US)

(72) Inventors: Jotheeswari Kothandaraman, Richland, WA (US); Johnny Saavedra Lopez, Richland, WA (US); Yuan Jiang, Richland, WA (US); Robert A. Dagle, Richland, WA (US); David J. Heldebrant, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 615 days.

(21) Appl. No.: 18/354,571

(22) Filed: Jul. 18, 2023

(65) Prior Publication Data

US 2025/0026700 A1 Jan. 23, 2025

(51) Int. Cl.

| | |
|---|---|
| ***C07C 29/153*** | (2006.01) |
| ***B01D 53/14*** | (2006.01) |
| ***B01D 53/62*** | (2006.01) |
| ***B01D 53/78*** | (2006.01) |
| ***B01J 21/06*** | (2006.01) |
| ***B01J 23/10*** | (2006.01) |

(Continued)

(52) U.S. Cl.

CPC ........ *C07C 29/153* (2013.01); *B01D 53/1475* (2013.01); *B01D 53/1493* (2013.01); *B01D 53/62* (2013.01); *B01D 53/78* (2013.01); *B01J 21/063* (2013.01); *B01J 23/10* (2013.01); *B01J 23/42* (2013.01); *B01J 23/63* (2013.01); *C01B 32/40* (2017.08); *B01D 2252/202* (2013.01); *B01D 2252/2041* (2013.01); *B01D 2252/20426* (2013.01); *B01D 2252/20431* (2013.01); *B01D 2252/20452* (2013.01); *B01D 2252/504* (2013.01); *B01D 2257/504* (2013.01)

(58) Field of Classification Search

CPC ... C07C 29/153; C01B 32/40; B01D 53/1475; B01D 53/1493; B01D 53/62; B01D 53/78; B01D 2252/202; B01D 2252/2041; B01D 2252/20426; B01D 2252/20431; B01D 2252/20452; B01D 2252/504; B01D 2257/504; B01J 21/063; B01J 23/10; B01J 23/42; B01J 23/63

See application file for complete search history.

(56) References Cited

U.S. PATENT DOCUMENTS

| | | | |
|---|---|---|---|
| 10,961,173 B2 | 3/2021 | Kothandaraman et al. | |
| 11,492,302 B2 | 11/2022 | Kothandaraman et al. | |
| 2021/0214287 A1* | 7/2021 | Kothandaraman et al. | C07C 1/12 |

OTHER PUBLICATIONS

ACS Catal. 2022, 12, 15097-15109 (Graciani et al.) (Year: 2022).*

(Continued)

*Primary Examiner* — Amy C Bonaparte
*Assistant Examiner* — Derek Rhoades
(74) *Attorney, Agent, or Firm* — Derek H. Maughan; Frank Rosenberg

(57) ABSTRACT

An efficient and selective catalyst for the condensed phase hydrogenation of captured $CO_2$ in the presence of an advanced water-lean post combustion capture solvent, EEMPA. Selected heterogenous catalysts for suppress N-methylation of the capture solvent; especially a noble metal on a reducible metal oxide support is highly selective for C—N cleavage to produce methanol.

20 Claims, 15 Drawing Sheets

(51) Int. Cl.
*B01J 23/42* (2006.01)
*B01J 23/63* (2006.01)
*C01B 32/40* (2017.01)

(56) References Cited

OTHER PUBLICATIONS

Walter, E. D. et al., "Operando Mas Nmr Reaction Studies at High Temperatures and Pressures", The Journal of Physical Chemistry C, 122(15) (2018) 8209-8215.
He, K. & Wang, Q. "Activation of Pt Nanoclusters on TiO2 via Tuning the Metallic Sites to Promote Low-Temperature CO Oxidation", Catalysts 2021, 11, 1280.
Liu, J. et al., "Tackling CO Poisoning with Single-Atom Alloy Catalysts", Journal of the American Chemical Society, 138(20) (2016) 6396-6399.
Rödl, A.et al., "Assessment of Selected Hydrogen Supply Chains-Factors Determining the Overall GHG Emissions", In Hydrogen Supply Chains, Academic Press, San Diego, CA (2018) pp. 81-109.
https://www.parrinst.com/products/stirred-reactors/series-4560-100-600-ml-mini-reactors/ (accessed: Oct. 2023).
https://www.un.org/en/climatechange/net-zero-coalition (accessed: Oct. 2023).
Al-Mamoori, A.et al., "Carbon Capture and Utilization Update. Energy Technology", 5(6)(2017) 834-849.
Gabrielli, P. et al., "The Role of Carbon Capture and Utilization, Carbon Capture and Storage, and Biomass to Enable a Net-Zero-CO2 Emissions Chemical Industry", Industrial & Engineering Chemistry Research, 59(15) (2020) 7033-7045.
Eclaire, J., & Heldebrant, D. J. A call to (green) arms: a rallying cry for green chemistry and engineering for CO2 capture, utilisation and storage. Green Chemistry 20 (2018) 5058.
Ra, E. C., et al., "Recycling Carbon Dioxide through Catalytic Hydrogenation: Recent Key Developments and Perspectives", ACS Catalysis 10, (2020)11318.
Bui, M., et al., "Carbon capture and storage (CCS): the way forward", Energy & Environmental Science, 11(5) (2018) 1062-1176.
Hepburn, C. et al.,"The technological and economic prospects for CO2 utilization and removal", Nature, 575(7781) (2019) 87-97.
National Academies of Sciences, Engineering, and Medicine, "Negative Emissions Technologies and Reliable Sequestration: A Research Agenda", The National Academies Press, Washington DC 2019. https://nap.nationalacademies.org/download/25259 (accessed: Oct. 2023).
Baylin-Stern, "Is carbon capture too expensive?" https://www.iea.org/commentaries/is-carbon-capture-too-expensive (accessed: Oct. 2023).
Wang, X. & Song, C., "Carbon Capture From Flue Gas and the Atmosphere: A Perspective", Front. Energy Res. 2020, 8, 560849.
https://www.iea.org/reports/ccus-in-clean-energy-transitions (accessed: Oct. 2023).
Keith, D. W. et al., "A Process for Capturing CO2 from the Atmosphere", Joule 2018, 2, 1573.
Aaron, D., & Tsouris, C. "Separation of CO2 from Flue Gas: A Review", Separation Science and Technology, 40 (1-3) I(2005) 321-348.
Luis, P., "Use of monoethanolamine (MEA) for CO2 capture in a global scenario: Consequences and alternatives", Desalination 380 (2016) 93-99.
Heldebrant, D. J. et al., "Water-Lean Solvents for Post-Combustion CO2 Capture: Fundamentals, Uncertainties, Opportunities, and Outlook", Chemical Reviews, 117(14) (2017) 9594-9624.
Lao, D. B. et al., "The steps of activating a prospective CO2 hydrogenation catalyst with combined CO2 capture and reduction", Green Chemistry, 18(18) (2016) 4871-4874.
Kothandaraman, J. et al., "Condensed-Phase Low Temperature Heterogeneous Hydrogenation of CO2 to Methanol", Catalysis Science & Technology, 8 (2018) 5098.
Subramani, V. et al., "A Review of Recent Literature to Search for an Efficient Catalytic Process for the Conversion of Syngas to Ethanol", Energy & Fuels, 22(2) (2008) 814-839.
Kar, S. , Goeppert.S, et al., "Integrated CO2 Capture and Conversion to Formate and Methanol: Connecting Two Threads", Acc. Chem. Res. 52, 10 (2019) 2892-2903.
Rezayee, N. M. et al., "Tandem Amine and Ruthenium-Catalyzed Hydrogenation of CO2 to Methanol", Journal of the American Chemical Society, 137(3) (2015) 1028-1031.
Kothandaraman, J., & Heldebrant, D. J. "Towards environmentally benign capture and conversion: Heterogeneous metal catalyzed CO2 hydrogenation in CO2 capture solvents", Green Chem. 2020, 22, 828.
Kothandaraman, J. et al., "Chemical transformations of captured CO2 into cyclic and polymeric carbonates", Journal of CO2 Utilization, 32 (2019) 196-201.
Kar, S. et al., "Manganese-Catalyzed Sequential Hydrogenation of CO2 to Methanol via Formamide", ACS Catalysis, (9) (2017) 6347-6351.
Scott, M. et al. "Methylformate from CO2: an integrated process combining catalytic hydrogenation and reactive distillation" Green Chem. 2019, 21, 6307.
Kothandaraman, J. & Heldebrant, D. J. "Catalytic coproduction of methanol and glycol in one pot from epoxide, CO2, and H2", RSC Advances, 10(69) (2020) 42557-42563.
Sternberg, A. et al., "Life cycle assessment of CO2-based C1-chemicals", Green Chemistry, 19(9) (2017) 2244-2259.
Klankermayer, J., & Leitner, W. "Love at second sight for CO2 and H2 in organic synthesis", Science, 350 (6261) (2015) 629-630.
Olah, G. A. et al., "Chemical Recycling of Carbon Dioxide to Methanol and Dimethyl Ether: From Greenhouse Gas to Renewable, Environmentally Carbon Neutral Fuels and Synthetic Hydrocarbons", The Journal of Organic Chemistry, 74(2) (2009) 487-498.
Olah, G. A. et al., "Anthropogenic Chemical Carbon Cycle for a Sustainable Future", Journal of the American Chemical Society, 133(33) (2011) 12881-12898.
Kothandaraman, J. et al., "Integrated Capture and Conversion of CO2 to Methane using a Water-lean, Post- Combustion CO2 Capture Solvent", ChemSusChem 2021, 14, 4812.
Kothandaraman, J. et al., "Conversion of CO2 from Air into Methanol Using a Polyamine and a Homogeneous Ruthenium Catalyst", J. Am. Chem. Soc. 2016, 138, 778.
Porosoff, M. D. et al., "Catalytic reduction of CO2 by H2 for synthesis of CO, methanol and hydrocarbons: challenges and opportunities", Energy Environ. Sci. 2016, 9, 62.
Kar, S. et al., "Advances in catalytic homogeneous hydrogenation of carbon dioxide to methanol", J. CO2 Util. 2018, 23, 212-218.
Kar, S. et al., Mechanistic Insights into Ruthenium-Pincer-Catalyzed Amine-Assisted Homogeneous Hydrogenation of CO2 to Methanol. Journal of the American Chemical Society, 141(7) (2019) 3160-3170.
Jiang, Y. et al., "Techno-Economic Comparison of Various Process Configurations for Post-Combustion Carbon 2 Capture Using a Single-Component Water-Lean Solvent", Int. J. Greenhouse Gas Control 2021, 106, 103279.
Zheng, F. et al. "A Single-Component Water-Lean Post-Combustion CO2 Capture Solvent with Exceptionally Low Operational Heat and Total Costs of Capture—Comprehensive Experimental and Theoretical Evaluation", Energy Environ. Sci. 2020, 13, 4106.
Gredig, S. V. et al., "Synthesis of methylamines from carbon dioxide and ammonia", Journal of the Chemical Society, Chemical Communications, (1) (1995) 73.
Gredig, S. V. et al. "Synthesis of methylamines from CO2, H2 and NH3. Catalytic behaviour of various metal-alumina catalysts", Applied Catalysis A: General, 162(1-2) (1997) 249-260.
Xie, Y. et al., "Heterogeneously catalyzed selective hydrogenation of amides to alcohols and amines". Catal. Sci. Technol. 2018, 8, 2784.
Gnanamani, M. K. et al., "Effect of pretreatment conditions on acidity and dehydration activity of CeO2—MeOx catalysts", Appl. Catal., A 2020, 602, 117722.

(56) References Cited

OTHER PUBLICATIONS

Kaithal, A. et al., "Acceptorless Dehydrogenation of Methanol to Carbon Monoxide and Hydrogen using Molecular Catalysts", Angew. Chem., Int. Ed. 2021, 60, 26500.
Shen, W. J. et al., "Low-temperature methanol decomposition to carbon monoxide and hydrogen catalysed over cationic palladium species in Pd/CeO2", Phys. Chem. Chem. Phys. 2000, 2, 1519.
Liu, Y. et al., "Methanol decomposition to synthesis gas at low temperature over palladium supported on ceria-zirconia solid solutions", Applied Catalysis A: General, 210(1-2) (2001) 301-314.
Brown, J. "Hydrogen production from methanol decomposition over Pt/Al2O3 and ceria promoted PI/Al2O3 catalysts", Catalysis Communications, 5(8) (2004) 431-436.
Li, G. et al., "Hydrogen production from methanol decomposition using Cu—Al spinel catalysts", Journal of Cleaner Production, 183 (2018) 415-423.
Toyao, T. et al., "Esterification of Tertiary Amides by Alcohols Through C—N Bond Cleavage over CeO2", Chem. Cat. Chem. 2018, 11, 449.
Bagheri, S. et al. Titanium Dioxide as a Catalyst Support in Heterogeneous Catalysis. The Scientific World Journal, 2014, (2014) 1-21.
Talukdar, A. K. et al., "Hydrogenation of phenol over supported platinum and palladium catalysts", Applied Catalysis A: General, 96(2) (1993) 229-239.
Spivey, J. J. et al., "Heterogeneous catalytic synthesis of ethanol from biomass-derived syngas", Chemical Society Reviews, 36(9) (2007) 1514.
Wang, D. et al., "Direct synthesis of ethanol via CO2 hydrogenation using supported gold catalysts", Chem. Commun. 2016, 52, 14226.

* cited by examiner

(A) Gas-phase methanol synthesis

(B) Condensed-phase methanol synthesis

2 EEMPA

COMBINED CAPTURE AND CONVERSION OF CO2 TO METHANOL IN A POST COMBUSTION CAPTURE SOLVENT

STATEMENT REGARDING FEDERALLY-SPONSORED RESEARCH AND DEVELOPMENT

This invention was made with Government support under Contract DE-AC0576RL01830 awarded by the U.S. Department of Energy. The Government has certain rights in the invention.

Introduction

Continuous anthropogenic emissions of $CO_2$ into the atmosphere since the industrial revolution have been associated with the ongoing environmental issues such as global warming and climate change. While we transition from fossil energy to renewable energy sources to reduce the $CO_2$ emissions, massive deployment of carbon capture, utilization, and storage (CCUS) technologies are needed to limit the global temperature rise (1.5-2 °C). Thus, direct air capture and flue gas capture technologies have been gaining considerable attention lately. Compared to direct air capture (containing ~400 ppm $CO_2$), post-combustion $CO_2$ capture from industrial flue gas (containing 5-15% $CO_2$) is an efficient and economic approach to curtail the emissions to the atmosphere from industrial sources, such as fossil-powered power plants, cement, and steel industries. Particularly, the solvent based post-combustion $CO_2$ capture technologies using amines (e.g., monoethanolamine) have been adopted commercially.

Upon the release of the captured $CO_2$ via thermal regeneration of the capture solvent, the $CO_2$ can either be stored underground for permanent $CO_2$ storage or it can be used as a $C_1$ source to produce value-added chemicals/materials and fuels, such as formic acid, methanol, methane, ethanol, polycarbonates, and others. However, the overall process of capture, compression, transportation, and storage is not energy efficient and cost effective. To overcome these challenges, the integrated capture and conversion of captured $CO_2$ to materials (IC$^3$M) has been developed. In the conventional CCUS approach, the cost of the capture process is mostly dominated by the energy intensive regeneration of the capture solvent. In the IC$^3$M approach, the exothermic conversion process partially offsets the energy required for the regeneration of the capture solvent. In addition, because the captured $CO_2$ is converted directly in the capture solvent medium, there is also energy saved on the $CO_2$ compression and transportation, thus reducing additional energy inputs, and associated equipment cost. In the IC$^3$M process, $CO_2$ is directly converted to methanol on the IC$^3$M solvent avoiding energy-intensive mechanical compression of the $CO_2$. By reducing the need for these additional energy inputs, and the associated equipment, IC$^3$M becomes a viable technology for modular distributed-scale processing platforms, which in turn could enable distributed applications such as the separation and conversion of $CO_2$ from landfill gases, wastewater treatment gases, and manure off-gas. Other sources of $CO_2$ may include, but are not limited to, fermenters, cement plants, steel kilns, and pulp and paper mills. Stranded hydrogen sources are also more likely to be co-sourced when considering distributed processing, which could enable lower cost/renewable hydrogen supplies in many applications.

Among the $CO_2$ derived value-added chemicals, methanol is most attractive as a fuel and a chemical feedstock to produce olefins, aromatics, and other chemicals. Currently, methanol is produced industrially from $CO_2$/CO and $H_2$ mixture using a ternary copper-based catalyst (Cu/ZnO/$Al_2O_3$) catalyst in the gas phase at high reaction temperature (>200 °C) and pressure (70-100 bar). In traditional gas phase catalysis, there are three proposed mechanisms involving (a) formate (HCOO*) intermediate, (b) CO* intermediate via reverse water gas shift mechanism (RWGS), and (c) trans-hydrocarboxyl (COOH). These intermediates are suggested depending on the catalysts and conditions (FIG. 1. (A), formate and CO pathways).[1] In the condensed phase hydrogenation in the presence of amine-based capture solvent, the intermediates involved are ammonium carbamate, formate and N-formamide (FIG. 1, (B)). The final hydrogenation of the N-formamide intermediate can form many products such as methane, methanol and N-methylation of the capture solvent. The N-methylation of the capture solvent causes solvent deactivation and thereby the active —NH— unit of the capture solvent is unavailable for subsequent reuse for $CO_2$ capture. The C—N cleavage of the N-formamide intermediate form methane or methanol, while the C—O cleavage cause N-methylation.

Despite these and other efforts, there remains a need in the industry to develop cost-effective, environmentally friendly $CO_2$ conversion catalyst systems that are commercially viable.

SUMMARY OF THE INVENTION

C—N cleavage of the N-formamide intermediate forms methane or methanol, while C—O cleavage causes N-methylation. See FIG. 1. Upon evaluating various metal with different supports, we identified that metals, particularly noble metals on reducible metal oxide supports such as $CeO_2$ and $TiO_2$ to be particularly selective for C—N cleavage to produce methanol, which was supported by operando $^{13}$C NMR studies.

We have demonstrated an integrated capture and utilization approach to produce methanol directly from the captured $CO_2$ inside an economically viable water-lean post-combustion capture solvent, that in time, may achieve cost parity with fossil-derived methanol. We have identified that traditional gas-phase $CO_2$ hydrogenation catalysts deactivated the solvent via N-methylation of the 2° amine moiety. We discovered that the Pt catalysts on reducible metal oxides (such as $TiO_2$ or $CeO_2$) suppress undesirable N-methylation of the capture solvent, showing high selectivity for C—N bond cleavage. The most promising catalyst, Pt/$TiO_2$, with its known favorable chemical stability in organic solvents, strong metal-support interaction, and acid-base properties were further evaluated under continuous-flow operation, which produced a single-pass $CO_2$ conversion of 29% with 70% selectivity to methanol at 170 °C Further increase in the reaction temperature to 190 °C resulted in a decrease in methanol selectivity with an unprecedented single-pass $CO_2$ conversion of 86%. The high single pass conversion achieved here is important as the solvent looping strategy to get higher conversion is not economical. Technoeconomic analyses (TEA) performed on the current state of this integrated technology showed that the methanol production cost is ~$1000/mt using $CO_2$ captured from flue gas from a 550 MW natural gas combined cycle (NGCC) plant. This cost is lower than the current renewable methanol cost of ~$1600/mt. Selectivity % refers to mol % throughout all the descriptions.

In one aspect, the invention provides a method of converting $CO_2$ to methanol comprising: contacting a solution comprising $CO_2$ in an amine sorbent over a solid catalyst comprising a noble metal on a reducible metal oxide support at a temperature in the range of 181 °C to 225 °C; wherein the $CO_2$ is post or pre combustion $CO_2$; and wherein the conversion of $CO_2$ occurs in a condensed phase and the $CO_2$ is converted to methanol with at least 40% selectivity; wherein the single pass conversion of $CO_2$ is at least 75%; and wherein the $C_{2+}$ alcohol selectivity, or the ethanol selectivity, is at least 4 mol %.

In another aspect, the invention provides a method of converting $CO_2$ comprising: providing continuous flow reactor system comprising: an absorber; a pump; and a reactor; enriching an amine sorbent with $CO_2$ by contacting the solvent with a flue gas comprising $CO_2$ to create a $CO_2$-enriched solution in the absorber; pressurizing the $CO_2$-enriched solution to between 30 and 100 bar $H_2$; heating the $CO_2$-enriched solution; producing a heated and pressurized $CO_2$-enriched solution; feeding the heated and pressurized $CO_2$-enriched solution with pressurized $H_2$ gas into a reactor comprising a solid catalyst comprising a noble metal on a reducible metal oxide support and reacting the solution over the solid catalyst at a temperature of between 181 and 225 °C; and producing a product solution in which the $CO_2$ in the solution is converted into methanol, $C_{2+}$ alcohols, $CH_4$, and light hydrocarbons over the solid catalyst.

In any of its aspects, the invention can be characterized by one or any combination of the following: further comprising one or any combination of the following: wherein the methanol selectivity is at least 50%; wherein the methanol selectivity is in the range of 40 to about 80%; wherein the single pass conversion of $CO_2$ is in the range of 75 to about 90%; wherein the selectivity to ethanol is 4 to 10 mol %; wherein the selectivity to butanol is at least 1.7 mol %; wherein the selectivity to butanol is about 2 to about 5 mol %; wherein the conversion of $CO_2$ is in a continuous flow operation; wherein the method occurs in a single pass; comprising a single pass $CO_2$ conversion of 80-90%; wherein the catalyst support comprises $CeO_2$ or $TiO_2$; wherein the amine sorbent is a water-lean solvent; further comprising separation and conversion of $CO_2$ from landfill gases, waste-water treatment gases, manure off-gas, fermenters, cement plants, steel kilns, and pulp and paper mills; wherein the amine sorbent is N-(2-EthoxyEthyl)-3-MorpholinoPropan-1-Amine (2-EEMPA); wherein the amine sorbent with 0.5-20 wt % $CO_2$ loading; wherein ethanol is a co-solvent; wherein CO and N-formamide are formed as intermediates; wherein the noble metal is Pt; wherein the solid catalyst comprises 0.1-20 wt % Pt, preferably 5-10 wt % Pt, on a $CeO_2$ or $TiO_2$ support; comprising a gas feed of 0.005-0.05 mL/min of $H_2/N_2$ gas; wherein the solid catalyst was pretreated in situ at 120 °C under a reducing flow of 30-65 sccm 10% $H_2$ in $N_2$; wherein the C—N cleavage selectivity is at least 50%, or preferably at least 80%, or between 85% and 100%; wherein the temperature is at least 185 °C or at least 190 °C, or in the range of 185 to 195 °C; comprising a single pass $CO_2$ conversion of 80-90%; wherein the conversion of $CO_2$ occurs in a condensed phase; wherein the solid catalyst comprises Pt disposed on a reducible metal oxide support; wherein the catalyst supports comprise $CeO_2$ and/or $TiO_2$; wherein the amine sorbent is a water-lean post-combustion solvent; comprising the separation and conversion of $CO_2$ from landfill gases, waste-water treatment gases, manure off-gas, fermenters, cement plants, steel kilns, and pulp and paper mills; wherein the amine sorbent is N-(2-EthoxyEthyl)-3-MorpholinoPropan-1-Amine (2-EEMPA); wherein the amine sorbent is a solvent with 2-15 wt % $CO_2$ loading; wherein ethanol is a co-solvent; wherein CO and N-formamide are formed as intermediates; wherein the noble metal is Pt; wherein the solid catalyst comprises 5-10 wt % Pt disposed on a $CeO_2$ or $TiO_2$ support; wherein the gas flow is between 0.005-0.05 mL/min; wherein the catalyst is 27-100% selective for C—N bond cleavage; wherein the $H_2$ that was not consumed in the reactor is separated from the product solution in a pressure swing adsorption unit and recycled back to the reactor; wherein the methane and other light hydrocarbons are separated from the product solution in a pressure swing adsorption unit and used as fuel gas; wherein the alcohols are separated and recovered from the product solution;

wherein the alcohols and water are separated from the product solution and one another using extractive distillation, wherein ethylene glycol is used as an entrainer; wherein the $CO_2$-enriched solution contains 2-15% $CO_2$; and/or wherein the temperature is at least 185 °C or at least 190 °C.

In another aspect, the invention provides a composition of matter comprising an amine solvent, $CO_2$, and a heterogenous catalyst, and methanol derived from the carbon dioxide, wherein the methanol derived from the $CO_2$ makes up at least 1% of mass percent of the $CO_2$ and wherein the molar ratio of the methanol produced from $CO_2$ to ethyl formate in the composition is greater than 2.

The invention can be further characterized by one or any combination of the following features: wherein the catalyst suppresses N-methylation of capture solvent; the composition exists in the condensed phase; wherein the solvent is a water-lean post combustion solvent; wherein the solid catalyst comprises a noble metal disposed on a reducible catalyst support.

The invention also includes a system comprising any of the compositions and conditions described herein. The invention can be further elucidated in the examples below. The invention may be further characterized by any features in the examples, for example, any of the inventive aspects can be further characterized by values within ±20% (or within ±10%) of any of the values in any of the examples, tables or figures; however, the scope of the present invention, in its broader aspects, is not intended to be limited by these examples.

The invention is often characterized by the term "comprising" which means "including," and does not exclude additional components. In narrower aspects, the term "comprising" may be replaced by the more restrictive terms "consisting essentially of" or "consisting of."

Glossary

Absorber—A chamber adapted to provide space for contacting the amine solvent with the $CO_2$-containing gas.

Aliphatic—A substantially hydrocarbon-based compound, or a radical thereof (e.g., $C_6H_{13}$, for a hexane radical), including alkanes, alkenes, alkynes, including cyclic versions thereof (cycloaliphatic), and further including straight and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted.

Alkoxyalkyl—A radical having the general formula —RO—R' where R and R' independently are alkyl.

Amine—A compound including an amino group —N(R)R' where R and R'are independently hydrogen, alkyl, heteroalkyl, haloalkyl, aliphatic, heteroaliphatic, aryl (such as optionally substituted phenyl or benzyl), heteroaryl, alkylsulfano, or other functionality. A 1°, or primary, amine includes an $—NH_2$ group. A 2°, or secondary, amine includes an —N(H)R group. A 3°, or tertiary, amine includes an —N(R)R' group. A polyamine is an organic compound having more than two amino groups.

Amine Sorbent—A solvent containing an amine that is capable of retaining and releasing $CO_2$. The amine may comprise a 1° amine group, a 2° amine group, a 3° amine group, a pyridine, or any combination thereof. In any of the foregoing or following embodiments, the $CO_2$ may be adsorbed, absorbed, covalently, or ionically bound to the amine. In one embodiment, the sorbent comprises a 2° amine and a pyridine on the same molecule. In some embodiments, the amine comprises a polyamine, a tertiary amine, a compound according to Formula I, or any combination thereof, the compound according to Formula I having a structure $R^1(R^2)N-L^1-NH—R^3$ where each of $R^1$ and $R^2$ independently is aliphatic or cycloaliphatic or $R^1$ and $R^2$ together with the nitrogen to which they are attached form a heterocyclic ring, $L^1$ is aliphatic or cycloaliphatic or $L^1$ and $R^1$ together with the nitrogen to which they are attached form a heterocyclic ring, and $R^3$ is aliphatic, cycloaliphatic, cycloalkylalkyl or alkoxyalkyl.

Aromatic or aryl—A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

C—N bond cleavage selectivity—This measure is calculated using the following: C—N cleavage selectivity=(moles of methanol)×100/(moles of EEMPA-N-$CH_3$+moles of methanol). In the general case, EEMPA-N-$CH_3$ can be replaced by the sorbent.

$CO_2$-enriched—This is a relative term indicating that the substance has a higher concentration of $CO_2$ than a previous state. In preferred embodiments, a $CO_2$-enriched substance comprises at least 2 wt % $CO_2$ or at least 10 wt % $CO_2$, or in the range of 5-15 wt % $CO_2$.

$CO_2$-lean—This is a relative term indicating that the substance has a lower concentration of $CO_2$than the $CO_2$-enriched state. In some embodiments, less than 2 wt % $CO_2$, or in some embodiments 1 wt % or less.

Condensed phase—The term "condensed phase" refers to a liquid or solid phase, including liquid/liquid, liquid/solid, and solid/solid solutions and mixtures.

Heterocycle/Heterocyclic—A heterocycle or heterocyclic molecule comprises a 5-6 member ring wherein 4-5 member atoms are carbon atoms and 1-2 member atoms are heteroatoms, which may be sulfur, nitrogen, or oxygen, or any combination thereof.

Methanol selectivity—The mole % of converted $CO_2$ that was been converted into methanol. For example, if 2 moles of $CO_2$ have been consumed and 0.5 moles of methanol have been produced, then the selectivity is 25%.

Noble metal—Preferably, noble metals include gold, platinum, ruthenium, rhodium, palladium, osmium, iridium, and any combination thereof, but may also include copper and silver, and any combination of any of the above.

Reducible metal oxide support—The term "reducible oxides" is generally known to chemists interested in heterogeneous catalysis. Reducible oxides are solid state materials that are strongly affected by the reversible oxidation state of the metal. Transition metal oxides such as $CeO_2$ and $TiO_2$ are considered reducible oxides because the conditions required for thermodynamically favorable reducibility are attainable. On the other hand, for oxides such as $Al_2O_3$ and MgO, these conditions are quite extreme and therefore these catalyst supports are considered to be non-reducible. Reducible oxides include, but are not limited to $CeO_2$, $TiO_2$, $V_xO_y$, $Fe_xO_y$, $Co_xO_y$, $HfO_2$, $ZrO_2$, $MnO_x$, $PrO_x$, $SmO_x$, $MoO_3$, $WO_3$, $In_2O_3$, and more complex solids, such as $BaTiO_3$ and $LaCoO_3$, and any combination thereof.

Water-lean—Any water content below 1 mole of water per mole amine, or below 1 molar equivalent, or below 10 wt %, preferably 1-5 wt %. Water content is commonly below 10 wt %, but most water-lean solvents operated for the carbon capture at 5 wt % or below water content. Compared to the aqueous post-combustion solvents (e.g., aqueous 30 wt % monoethanol amine), water-lean post-combustion solvents are superior for the IC3M approach mostly due to the following advantages: (1) high $CO_2$ physical solubility in the water-lean organic solvent, thus requiring low $CO_2$ pressure and temperature for the conversion. Lowering the reaction temperature can also increase the conversion and selectivity in hydrogenation reactions because it can suppress the endothermic reverse water gas shift reaction (ΔH=41.2 KJ/mol), (2) In the case of $CO_2$ hydrogenation (to methane, methanol, ethanol, methyl formate and others) reactions involving water as a byproduct, the excess water in the aqueous solvents could reverse the equilibrium and could also block catalyst active sites, and (3) water-lean solvents are more resistant to corrosion and solvent decomposition.

Figure 8:
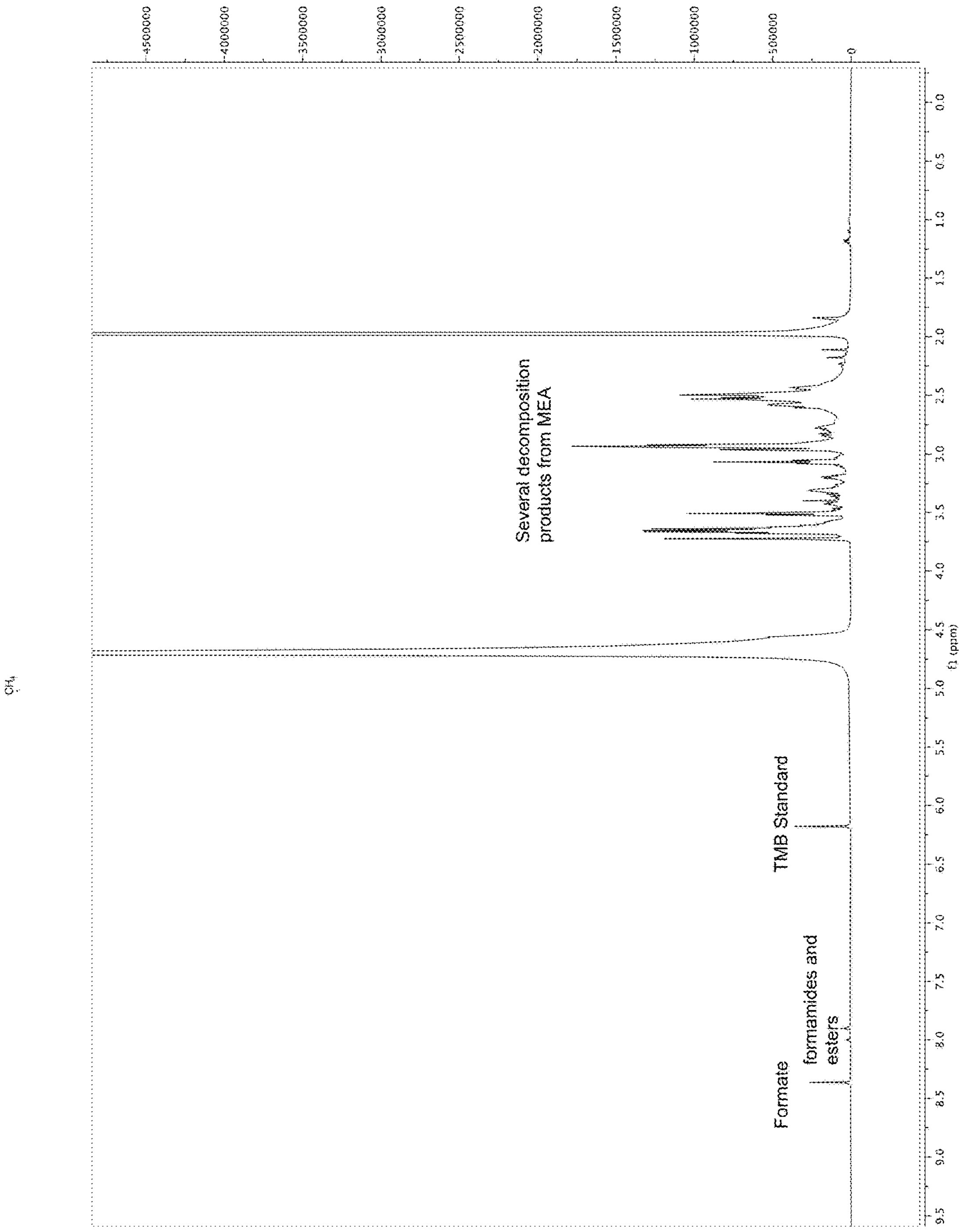

FIG. 8: $^1$H NMR of the crude reaction mixture (from Table 5, entry 8) in $CD_3CN$.

Figure 9:
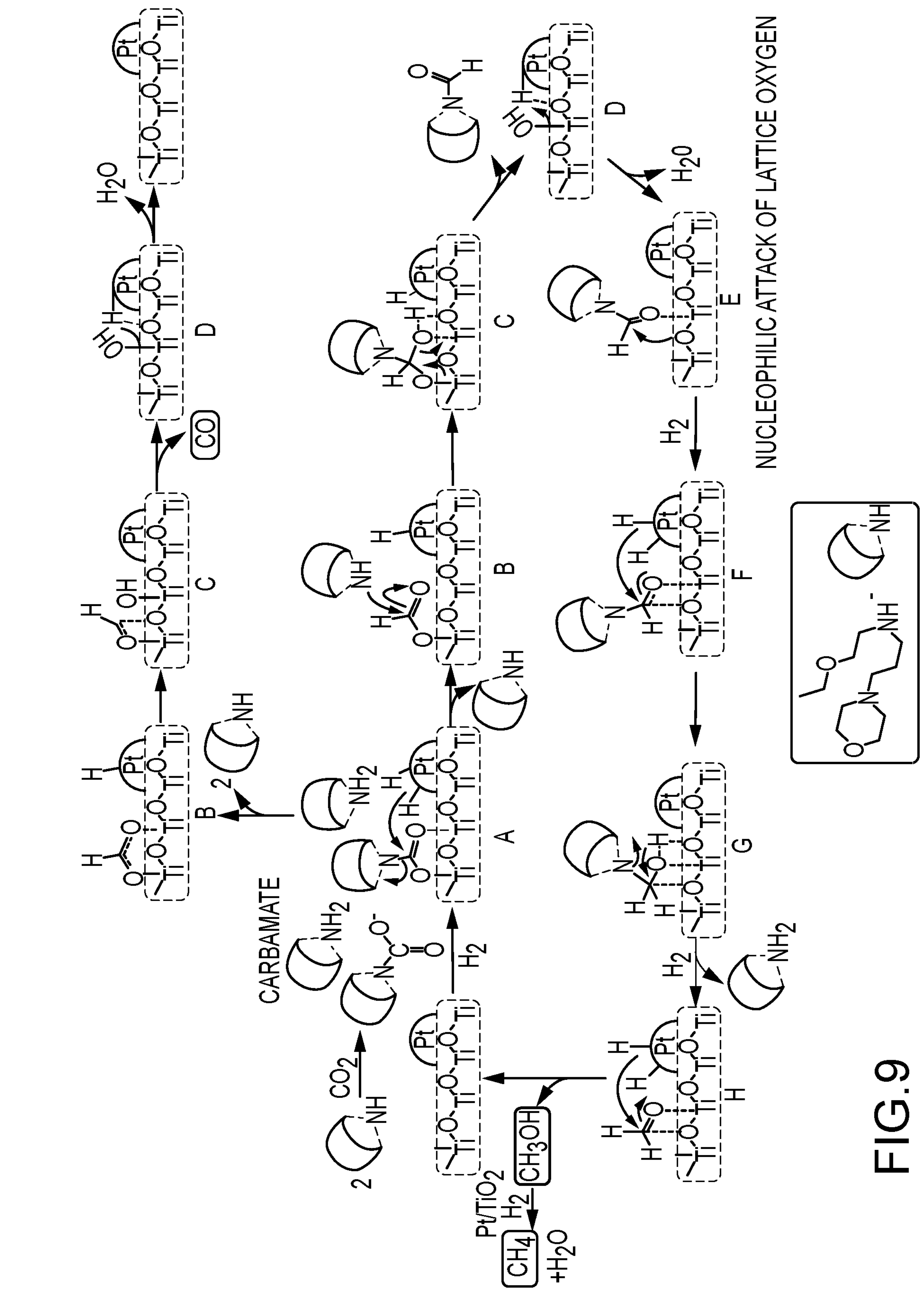

FIG. 9: Proposed reaction mechanism for the hydrogenation of captured $CO_2$ in the presence of $Pt/TiO_2$ catalyst. Surface hydroxyl groups are not shown for simplicity.

Figure 10:
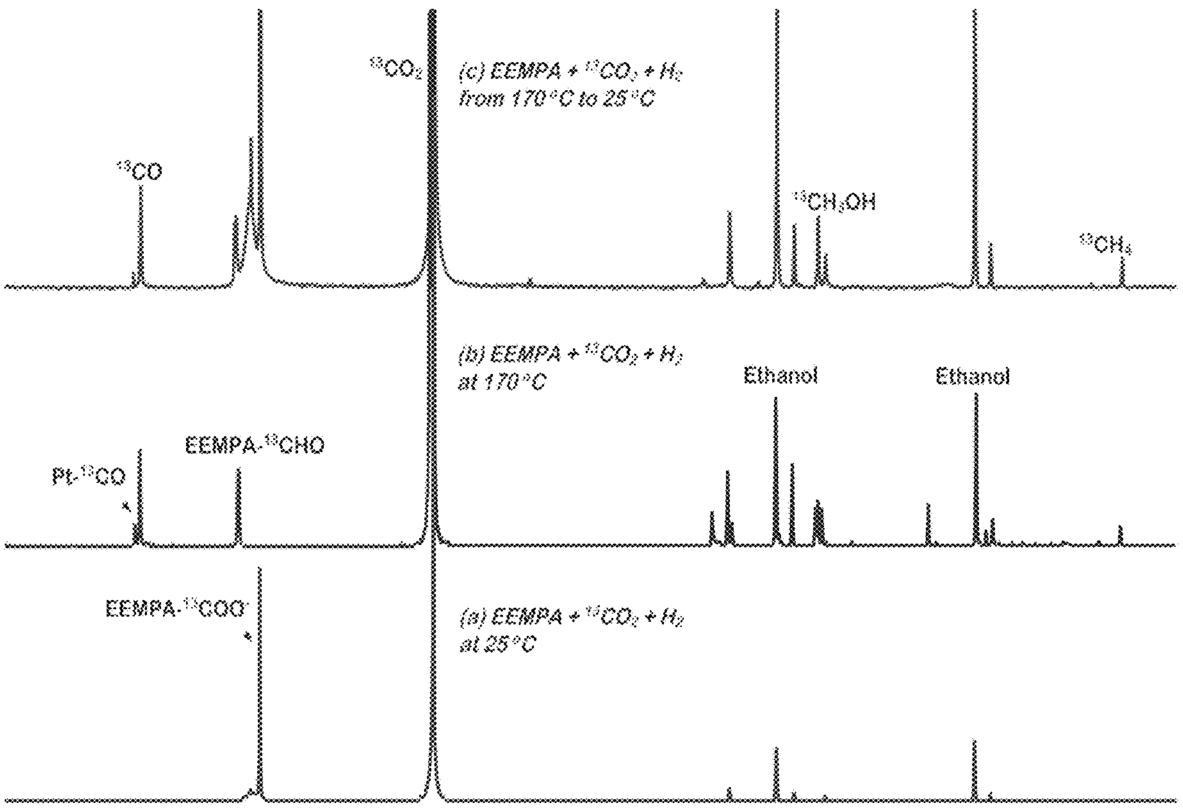

FIG. 10: In situ $^{13}$C MAS-NMR during the hydrogenation of $^{13}CO_2$ in the presence of 2-EEMPA and a 5wt % $Pt/TiO_2$ catalyst at 170 °C under 60 bar $H_2$ (initial pressure) in an ethanol co-solvent, 2-EEMPA:EtOH=1:10 (molar ratio).

Figure 11:
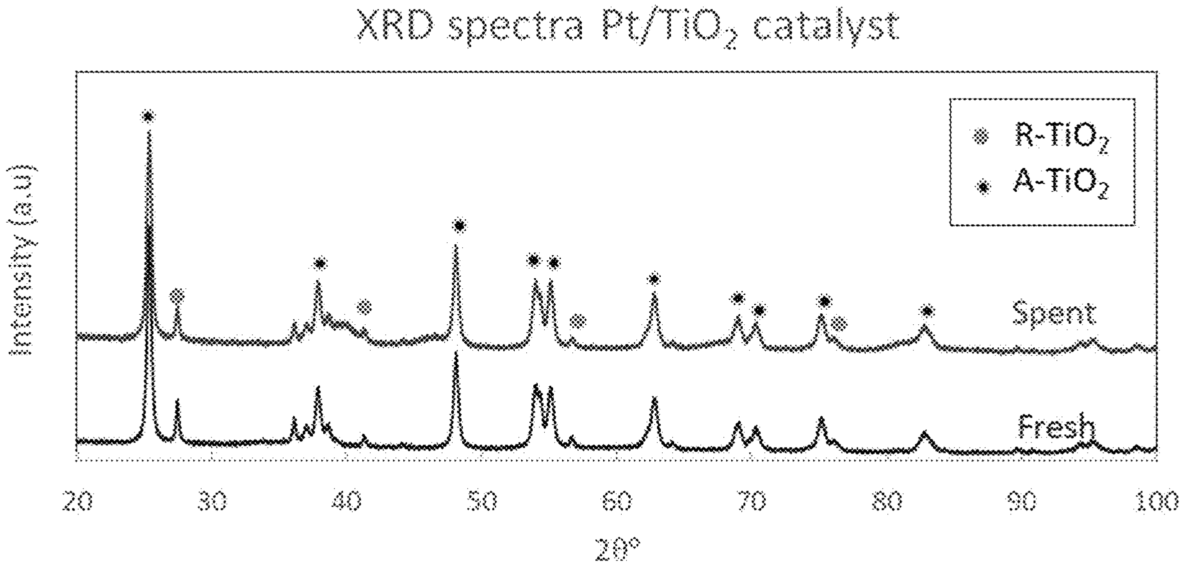

FIG. 11: XRD spectra of fresh and spent $Pt/TiO_2$ catalysts used in experiments in Table 8 (entries 6-8). (XRD=X-ray powder diffraction)

Figure 12:
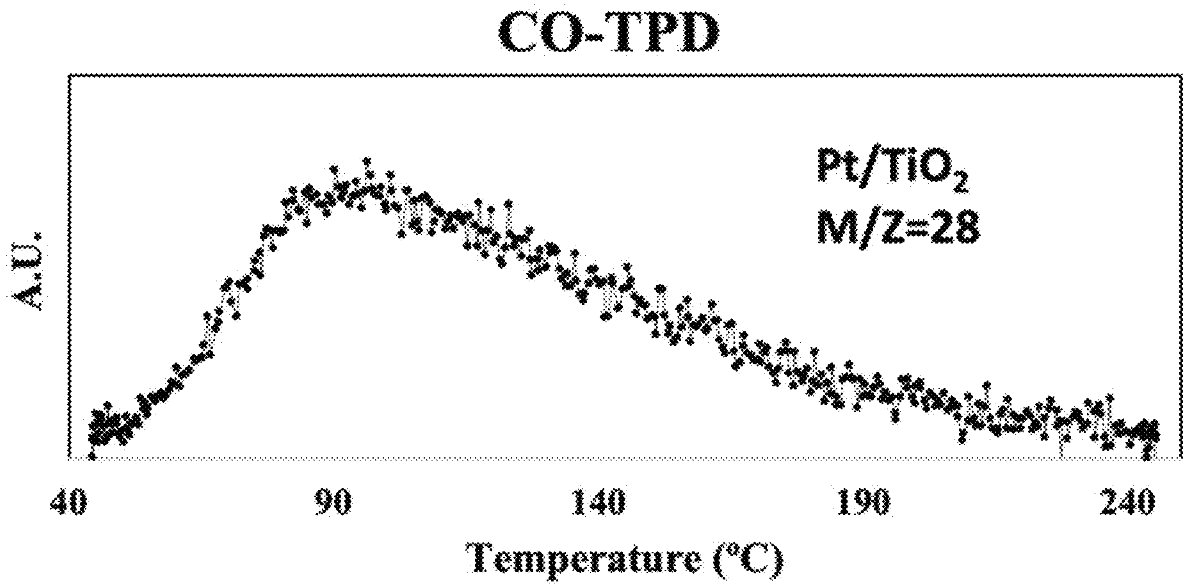

FIG. 12: CO-TPD for the $Pt/TiO_2$ catalyst (from Table 7, entry 1). TPD conditions: after CO chemisorption saturation at 40 °C, samples were purged under flowing He (25 sccm) for 10 min, then the samples were heated up to 250 °C at a rate of 10 °C/min in flowing He (25 sccm).

Figure 13:
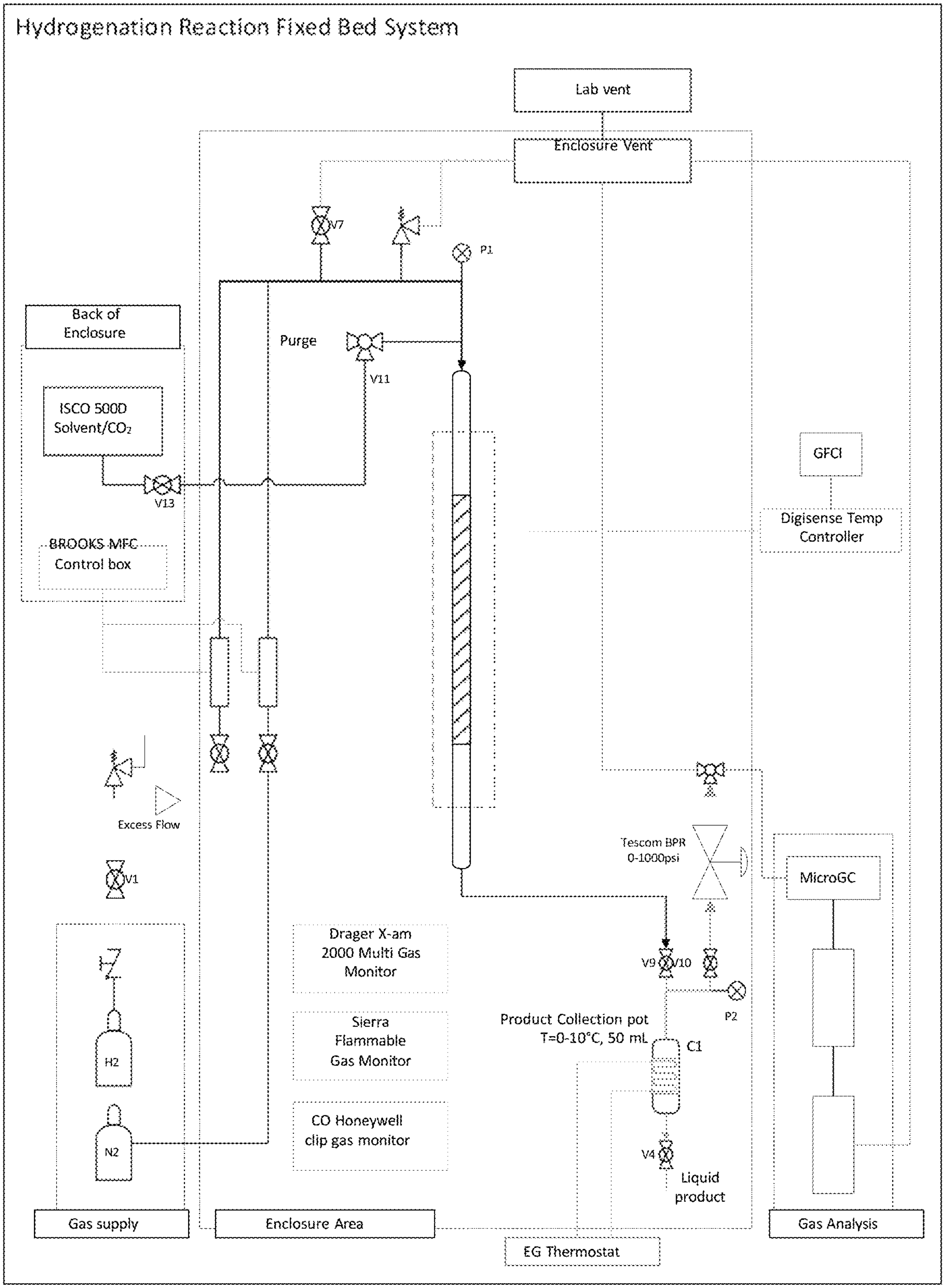

FIG. 13: Continuous flow reactor set up. Reaction setup consists of a downstream fixed bed reactor. Catalyst (1-5 g) was loaded inside a (⅜in) stainless steel tube, pressure was maintained using a Tescom back pressure regulator. Gases and liquid were fed using gas mass flow controllers (Brooks) and a syringe pump (ISCO Teledyne) (0-100 sccm and 0-1 mL/min, respectively). Liquid sample was collected periodically from a 50 mL collection pot downstream the reactor (50 mL, 0-10 °C). Gas sample was analyzed with a microGC instrument (Fusion Inficon).

Figure 14:
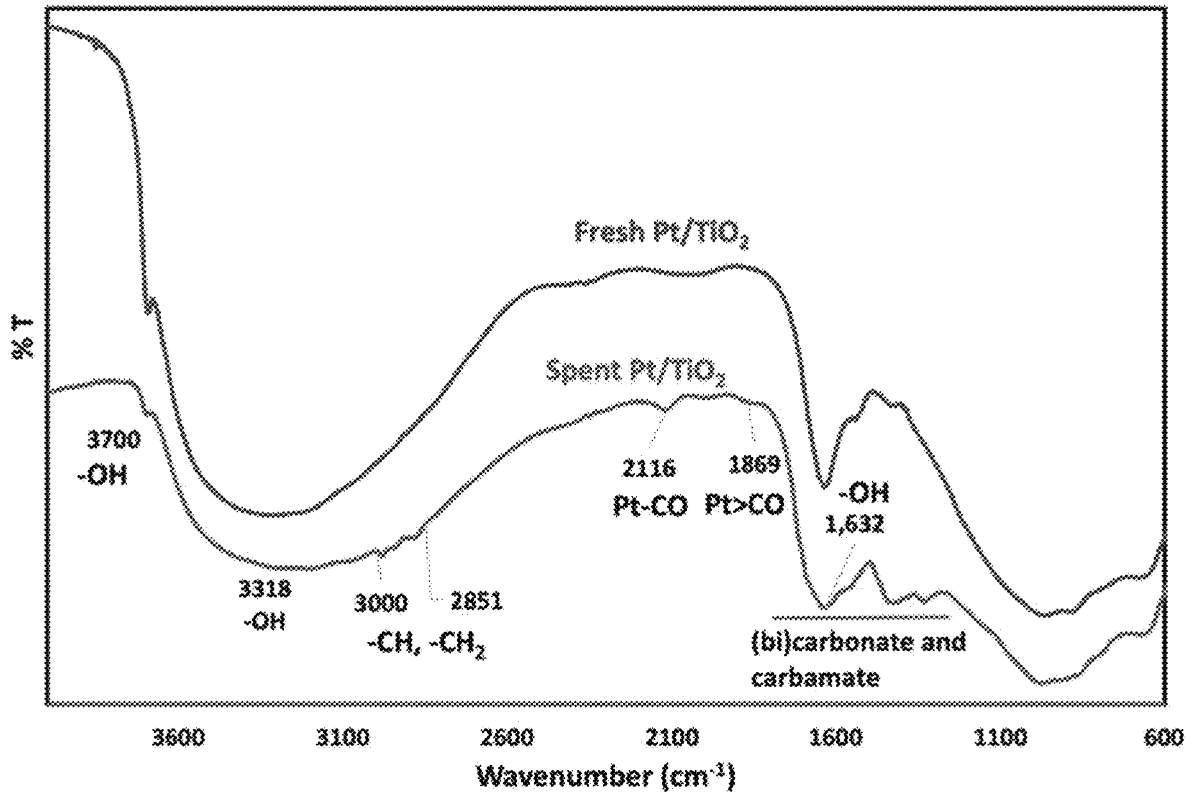

FIG. 14: Diffuse reflectance infrared Fourier Transform Spectroscopy (DRIFTS) spectra of fresh (blue spectrum, after post-synthesis calcination) and spent (red spectrum, collected from reactor after reaction) $Pt/TiO_2$ catalysts used in experiments presented in Table 7 (entries 6-8).

Figure 15:
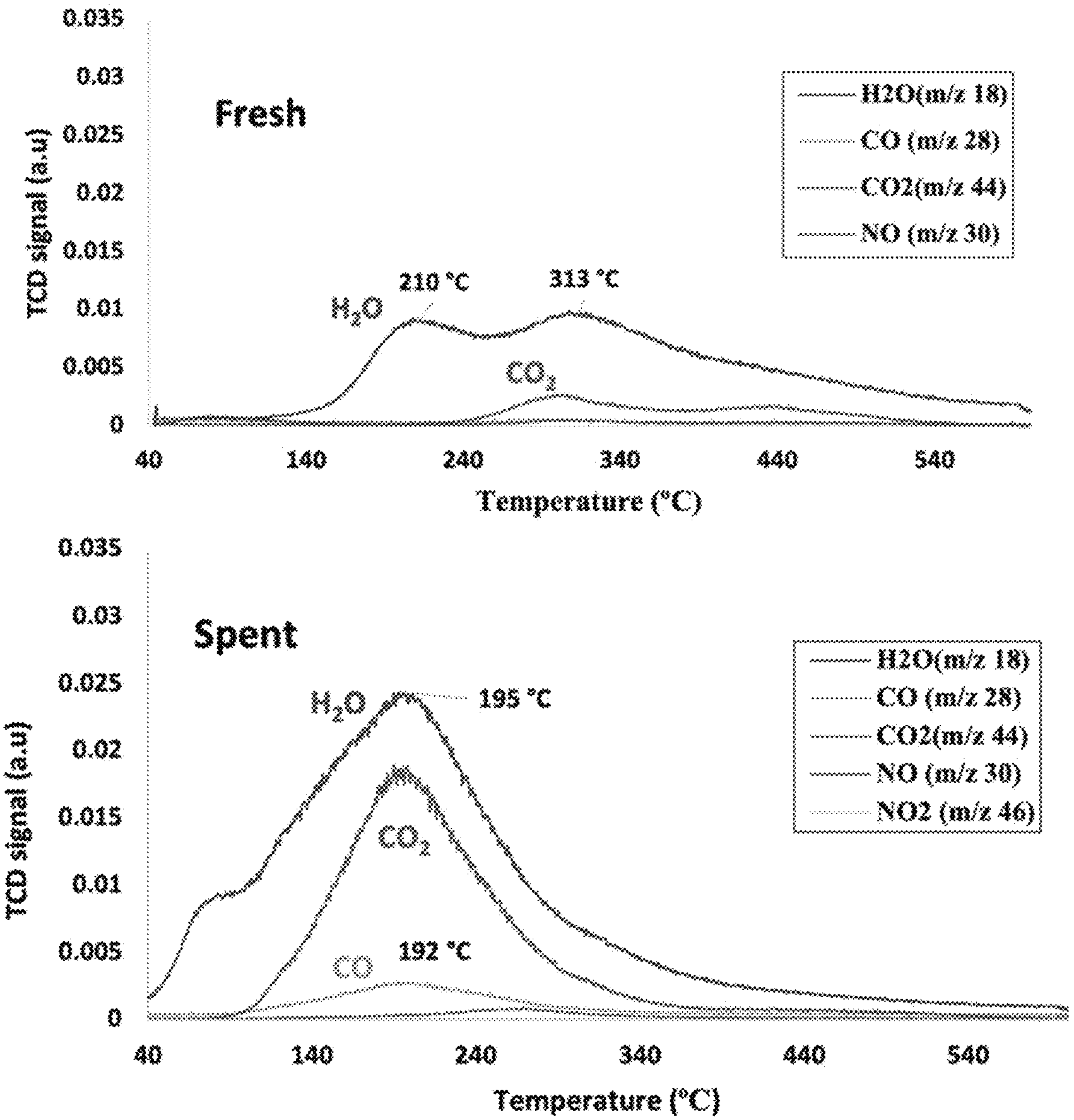

FIG. 15: TPO-MS profiles of the fresh and spent $Pt/TiO_2$ catalysts used in experiment ° C in Table 7 (entries 6-8). Using 50 sccm of a mixture of 10 % O2/He (50 cc $min^{-1}$), 50 mg of the samples were ramped to 600 °C (10 °C $min^{-1}$). (TPO-MS=temperature-programmed oxidation with mass spectrometry)

DETAILED DESCRIPTION OF THE INVENTION

The amine may comprise a polyamine, a tertiary amine, an alkanolamine, an aminopyridine, a diamine compound according to Formula I, or any combination thereof, the compound according to Formula I having a structure $R^1(R^2)$N-$L^1$-NH—$R^3$ where each of $R^1$ and $R^2$ independently is aliphatic or cycloaliphatic or $R^1$ and $R^2$ together with the nitrogen to which they are attached form a heterocyclic ring, $L^1$ is aliphatic or cycloaliphatic or $L^1$ and $R^1$ together with the nitrogen to which they are attached form a heterocyclic ring, and $R^3$ is aliphatic, cycloaliphatic, cycloalkylalkyl or alkoxyalkyl. In certain embodiments, the amine is not an amidine, since amidines may decompose under the reaction conditions.

$R^1(R^2)$N-$L^1$-NH—$R^3$ (Formula I)

With respect to Formula I, each of $R^1$ and $R^2$ independently is aliphatic, preferably alkyl, such as $C_{1-6}$alkyl, $C_{1-4}$alkyl, $C_{1-3}$alkyl, or $C_{1-2}$alkyl; cycloaliphatic, preferably cycloalkyl, such as $C_{3-7}$cycloalkyl or $C_{3-4}$cycloalkyl, and may be cyclopropyl; or $R^1$ and $R^2$ together with the nitrogen to which they are attached, form a heterocyclic ring, such as an non-aromatic heterocyclic ring, preferably a 5- or 6-membered heterocyclic ring and optionally comprising one or more additional heteroatoms, such as 1 or 2 heteroatoms selected from oxygen, nitrogen or sulfur, and/or optionally substituted with alkyl, such as $C_{1-4}$alkyl. Alternatively, $R^1$ may form a heterocyclic moiety, with $L^1$, such as a non-aromatic heterocyclic moiety, preferably a 5- or 6-membered heterocyclic moiety. In such embodiments, $R^2$ is aliphatic, preferably alkyl, such as $C_{1-6}$alkyl, $C_{1-4}$alkyl, $C_{1-3}$alkyl, or $C_{1-2}$alkyl, or cycloalkyl, such as $C_{3-7}$cycloalkyl.

Each of $R^1$ and $R^2$ independently is linear alkyl or branched alkyl, such as $C_{1-6}$linear alkyl, or $C_{3-6}$branched alkyl. Exemplary linear alkyl moieties include, but are not limited to methyl, ethyl, n-propyl or n-butyl, and exemplary branched alkyl moieties include, but are not limited to, isopropyl, tert-butyl, iso-butyl, or sec-butyl. And $R^1$ and $R^2$ may be the same or different. In other embodiments, $R^1$ and $R^2$ together with the nitrogen to which they are attached form a non-aromatic heterocyclic moiety, such as morpholine, thiomorpholine, piperidine, pyrrolidine, or piperazine, optionally substituted with $C_{1-4}$alkyl, typically, methyl, ethyl, isopropyl, or tert-butyl.

$L^1$ is aliphatic, preferably alkyl, such as $C_{2-4}$alkyl or $C_{2-3}$alkyl; cycloaliphatic, preferably cycloalkyl, such as $C_{5-7}$cycloalkyl; or $L^1$ and $R^1$ together with the nitrogen to which they are attached form a non-aromatic heterocyclic ring, such as a 5-, 6-, or 7-membered heterocyclic, optionally comprising one or more additional heteroatoms, such as 1 or 2 heteroatoms selected from oxygen, nitrogen or sulfur. In some embodiments, $L^1$ is —$CH_2CH_2$— or —$CH_2CH_2CH_2$—, but in other embodiments, $L^1$ and $R^1$ together with the nitrogen to which they are attached, form a 5- or 6-membered non-aromatic heterocyclic ring, such as a piperidine or pyrrolidine ring. In some such embodiments, $R^2$ is $C_{1-6}$alkyl, such as $C_{1-4}$alkyl, $C_{1-3}$alkyl, or $C_{1-2}$alkyl, preferably methyl or ethyl.

$R^3$ is aliphatic, cycloaliphatic, cycloalkylalkyl or alkoxyalkyl. In some embodiments, $R^3$ is alkyl, such as $C_{1-6}$alkyl, $C_{1-4}$alkyl, $C_{1-3}$alkyl, or $C_{1-2}$alkyl; cycloalkyl, such as $C_{3-7}$cycloalkyl or $C_{3-4}$cycloalkyl; cycloalkylalkyl, such as —$CH_2$cycloalkyl; or alkoxyalkyl, such as $C_{1-6}$alkyl, $C_{1-4}$alkyl, $C_{1-3}$alkyl, or $C_{1-2}$alkyl substituted $C_{1-4}$alkoxy, $C_{1-2}$alkoxy, or $C_{3-6}$cycloalkyl. $R^3$ may be linear or branched alkyl, and may be a linear $C^{1-6}$alkyl, $C_{1-4}$alkyl, $C_{1-3}$alkyl, or $C_{1-2}$alkyl or a branched $C_{3-6}$alkyl, $C_{3-4}$alkyl, or $C_3$alkyl. Exemplary linear and branched alkyl moieties include, but are not limited to, methyl, ethyl, n-propyl, or n-butyl, and isopropyl, isopropyl, tert-butyl, iso-butyl, or sec-butyl. In some embodiments, $R^3$ is unsubstituted, but in other embodiments, $R^3$ is substituted, and may be substituted with alkoxy, such as $C_{1-4}$alkoxy, or $C_{1-2}$alkoxy. Exemplary alkoxy substituents include, but are not limited to, methoxy, ethoxy, propoxy, isopropoxy or cycloalkoxy, such as cyclopropoxy.

Nonlimiting Exemplary compounds within the scope of Formula I include:

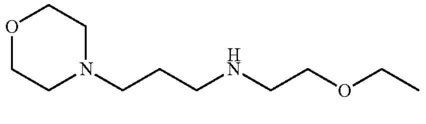
,

-continued

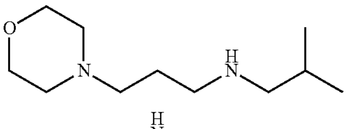,

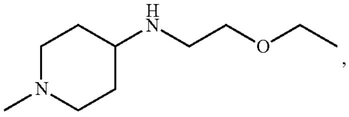,

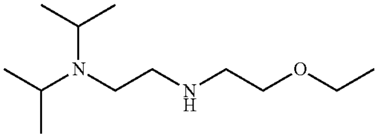,

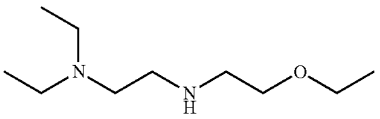,

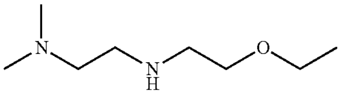,

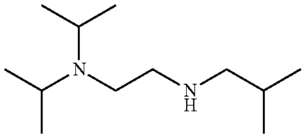,

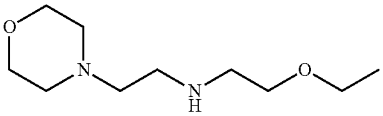,

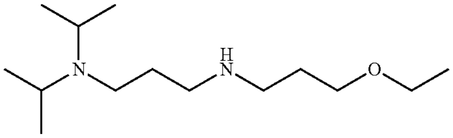,

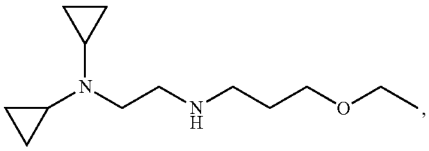,

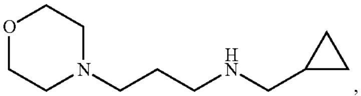,

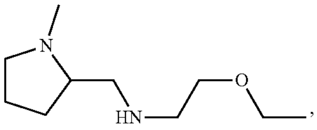,

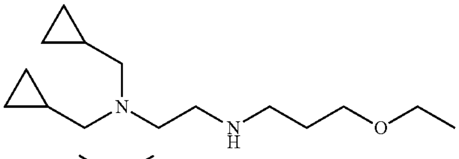,

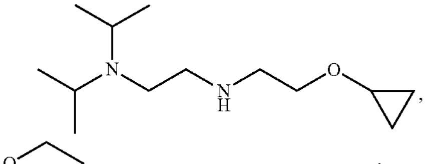,

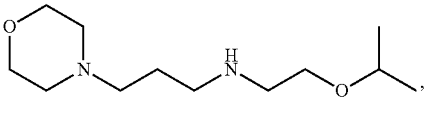, or

-continued

Figure 5:
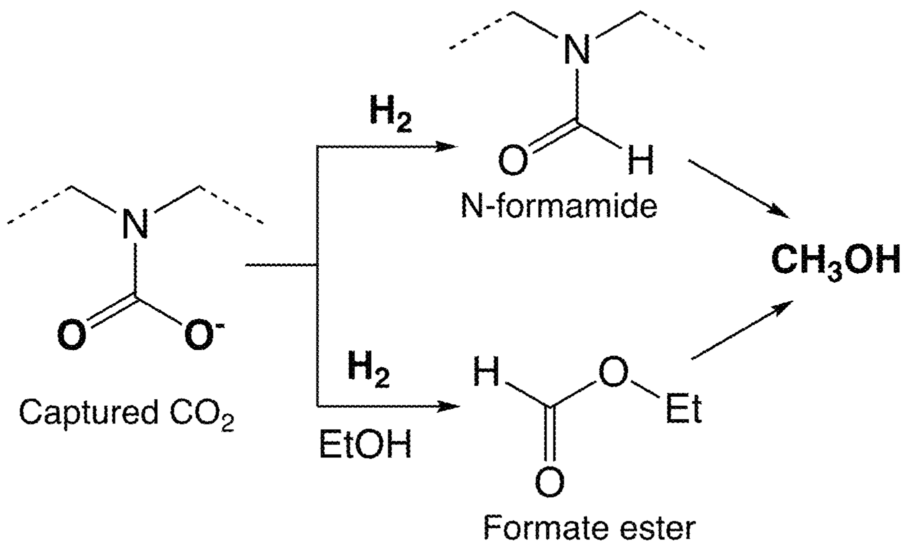
FIG. 5: Reaction mechanism with ethanol co-feed.

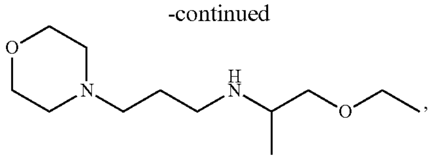,

The amine sorbent can be combined with a solvent, i.e. a co-solvent or co-feed, to form a liquid sorbent solution. The co-solvent or co-feed can be any alcohol-containing species, including but not limited to aliphatic, aromatic or other polymeric or polyols, or any combination thereof. For example, a preferred co-feed is ethanol. It was observed that an ethanol co-feed facilitates reaction through formate ester intermediate, which was more selective to methanol than N-formamide intermediate. (FIG. 5)

The catalyst used in the conversion of $CO_2$ to products comprises a noble metal disposed on a reducible oxide support. Preferably, the catalyst comprises from 1 to 20 wt % noble metal, more preferably 1 to 10 wt %. The noble metal can be any of the noble metals or any combination of the noble metals.

The catalyst may be described by any of the properties reported herein, or within ±30% or ±20% or ±10% of any of the measurements described herein.

Properties of Reaction

The reactions can be characterized by one or any combination of the following: an amine sorbent preferably with at least 2 wt %, or at least 5 wt %, or in the range of 3 to 15 wt % $CO_2$ loading; a reaction temperature of at least 140 °C, or preferably at least 160 °C, or in the range of 120 to 200 °C; a reaction pressure of at least 30 bar $H_2$, or preferably at least 50 bar $H_2$, or in the range of 30-100 bar $H_2$.

The reactions can be further characterized by one or any combination of the following: Selectivity to methanol from $CO_2$ is preferably at least 50%, or at least 60%, or in the range of 50 to about 95%, or 60 to about 95%. WHSV (weight hourly space velocity in units of g $CO_2$/g cat/h) of at least 0.005, or at least 0.010, or in the range of 0.010 to 0.50, or in the range of 0.010 to 0.20, or in the range of 0.010 to 0.10.

The catalyst and process were demonstrated to be selective towards methanol with 93% selectivity at 140 °C. At 190 °C, the $CO_2$ conversion increased from 12% to 86% when space velocity was decreased by a factor of 10. Conversion decreased from 86% to 65% over a span of approximately 40 hours.

Figure 3:
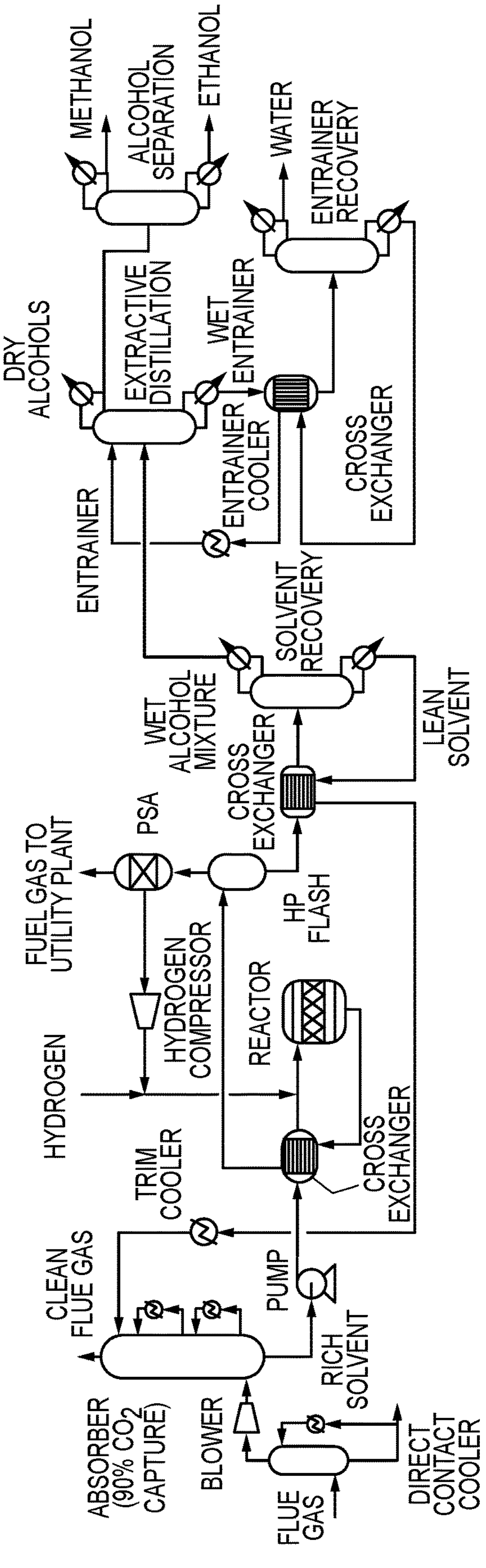
FIG. 3: Process flow diagram of the $IC^3M$ $CO_2$ capture and conversion to methanol process.
Figure 4:
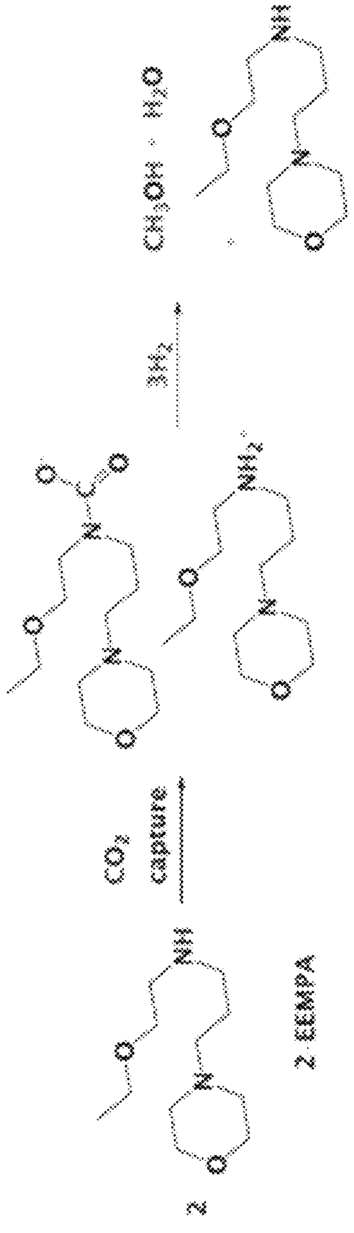
FIG. 4: Hydrogenation of captured $CO_2$ in the presence of Cu- and Ag-supported heterogeneous catalysts using a batch reactor system.

In FIG. 3, 90% $CO_2$ in the flue gas from a NGCC power plant is captured in the absorber by countercurrent contact with an amine sorbent solution, producing a $CO_2$-rich solvent. The condensed-phase $CO_2$-rich solvent is pumped to the desired pressure to avoid the use of a capital and energy-intensive $CO_2$ compressor. The pressurized $CO_2$-rich solvent is then heated and fed to the main reactor packed with $Pt/TiO_2$ catalyst at 190 °C, 60 bar along with $H_2$. In this analysis, $H_2$ is produced off-site from either fossil or renewable pathway, which is outside the system boundary. It is assumed that $H_2$ is delivered at the conversion plant at pressure as required for $H_2$ transportation.[31] The reactor product contains $CO_2$-lean solvent, unconverted $H_2$. methanol, $C_2$+ alcohols, $CH_4$, and light hydrocarbons. The product is first sent to a high-pressure flash drum, where the gas phase goes to the pressure swing adsorption (PSA) unit to separate unconverted $H_2$ from $CH_4$ and light hydrocarbons.

The $H_2$ is recycled back to the reactor, while $CH_4$ and light hydrocarbons are used as fuel gas to supply heat and energy for other unit operations. The liquid phase from the high-pressure flash drum is sent to the solvent recovery column to separate alcohols from the $CO_2$-lean solvent. The lean solvent from the bottom is recycled back to the absorber for $CO_2$ capture. Wet alcohols from the top contain mainly methanol, ethanol, and water. Because of the existence of azeotrope between these components, extractive distillation is used for alcohols and water separation, where ethylene glycol is used as an entrainer.

Materials and Analytical Techniques

Materials: 64 wt % $Cu/Zn/Al_2O_3$ was purchased from Alfa Acsar. 2-EEMPA was synthesized by following the procedure reported in the literature.[16a] Metal (Pt, Pd, Ni, Cu) supported on metal oxides ($TiO_2$, $Al_2O_3$, $CeO_2$, $SiO_2$, MgO) were prepared by incipient wetness impregnation of nitrate metal precursors followed by drying (8 h at 100 °C) and calcination at 400 °C (4 h under static air). Metal oxide supports: $TiO_2$=Degussa P25 from Sigma Aldrich, $Al_2O_3$=γ-$Al_2O_3$ from Engelhard, $CeO_2$=nanopowder (<25 nm) from Sigma Aldrich, $SiO_2$=Davisil 646 Silica gel from Sigma Aldrich, MgO=Nanoactive (R) MgO from Nanoscale Corporation. All other materials were purchased from commercial suppliers and used without further purification unless otherwise mentioned. All deuterated solvents were purchased from Cambridge Isotope Laboratories, Inc. 1,3,5-Trimethoxybenzene (TMB) was added as an internal standard for NMR spectroscopy.

The Cu/Zn/Al catalyst, which was derived from a hydrotalcite precursor with a $Cu^{2+}/Zn^{2+}$ atomic ratio of 2 (56% wt Cu), was prepared by a co-precipitation method at room temperature using nitrate precursors and a basic precipitation solution (2 m NaOH, 0.5 m $Na_2CO_3$). The precipitation product was aged (80 °C), washed, and dried overnight. The resulting precipitate hydroxide (layered hydroxide) was then calcined at 450 °C for 4 h to generate a combination of oxides.

Standard Procedure for Batch Experiments: A Parr reactor [34] (100 mL) equipped with a thermocouple, pressure transducer, and reactor controller, was charged with a catalyst and $CO_2$ loaded capture solvent and sealed in a $N_2$-atmosphere glovebox. The reactor was then pressurized with $H_2$ (60 bar) and heated to 170 °C. The reactor was cooled to room temperature, and the gas in the reactor headspace was analyzed using a 2-channel Fusion MicroGC (Inficon). The remaining excess gas was slowly released after cooling the reactor to −78 °C. TMB was dissolved in acetonitrile and added as an internal standard to the reaction mixture, and a small aliquot of the sample was analyzed by $^1H$ and $^{13}C$ NMR experiments in $CD_3CN$.

Procedure for In Situ High-Pressure and High-Temperature MAS-NMR: The MAS-NMR experiments were performed on an Agilent-Varian VNMRS NMR spectrometer equipped with a 7.05 T magnet, operating at 75.43 MHZ for the $^{13}C$ channel and 299.969 MHz for the $^1H$ channel, and using a 5 mm Chemmagnetics design HXY probe. The rotors were Varian/Agilent style cavern rotors (Revolution NMR LLC), modified for high-pressure samples as described previously.[35] 2-EEMPA (0.16 mmol), $Cu/ZnO/Al_2O_3$ or $Pt/TiO_2$ (8 mg), and ethanol (1.6 mmol) were transferred to a MAS-NMR rotor in a $N_2$-atmosphere glovebox. The rotor was charged with a $^{13}CO_2$ (0.28 mmol) and $H_2$ (0.8 mmol) at room temperature and heated to 170 °C. When the set temperature was reached, the rotor was kept at this temperature while an array of $^{13}C$ NMR spectra was collected. A 45° pulse was used. A recycle delay of 30 s and a spinning speed of 5 kHz were applied. The spectra were acquired with 64 scans and an acquisition time of 300 ms.

Standard Procedure for Continuous-Flow Experiments: Fixed-bed experiments were performed in a stainless-steel tubular reactor (3/8 nominal OD, 0.305 ID), the reactor wall was heated with a stainless-steel block (3 in) wrapped with a fiberglass heating tape (Omegalux) (FIG. 13). Liquid was fed to the reactor using a high-pressure Isco pump (Teledyne), and gases ($H_2$, $N_2$) were fed using mass flow controllers (Brooks). In a typical experiment, 1 g of catalyst (60-100 mesh) was loaded between quartz wool in the heated part of the reactor. Reaction conditions: pressure (60 bar) was controlled using a Tescom back pressure regulator, and temperature (120-190 °C) was controlled using a digisense R/S controller. After reaction, liquid products were condensed and collected in a stainless-steel 50 mL cylinder maintained at 0 °C using a recirculatory thermostat (VWR). Gas products were analyzed using a 4-channel Fusion MicroGC (Inficon), and liquid products were analyzed using liquid chromatography.

Catalysts Characterization: Fresh and spent samples of $Pt/TiO_2$ catalyst were studied using DRIFTS, TPO-MS, XRD, ICP, and CNHSO elemental analysis.

The DRIFTS accessory was a Harrick Praying Mantis with a reaction chamber and zinc selenide windows adapted to a Bruker IFS 66/S spectrometer. The spectra of the untreated samples were recorded with the sample at room temperature (21 °C) and at atmospheric pressure using a background with potassium bromide powder and dry nitrogen purge. The instrument resolution was 4 $cm^{-1}$ with an 8 mm aperture, and 1024 scans were co-added for the spectrum. A silicon carbide source was used with a KBr beam splitter and a liquid-nitrogen-cooled MCT detector. The scanner velocity was 60 kHz. The phase resolution was 32 $cm^{-1}$ with a Mertz phase correction. A Blackman-Harris-3-term apodization function was used with 2× zerofill. The nonlinearity correction was turned on.

TPO-MS was performed using a Micromeritics Autochem II 2920 chemisorption analyzer coupled with a Cirrus 2 Mass Spectrometer. 50 mg of sample was loaded under 50 sccm 10% $O_2$/He for 40 min, and without any preliminary thermal treatment, the sample was ramped up to 600 °C at a rate of 10 °C $min^{-1}$ and held at this temperature for 20 min. Effluent gases were monitored using mass spectrometry.

TPD and CO Chemisorption were performed using a Micromeritics Autochem II 2920 chemisorption analyzer. 100 mg of sample was loaded and was purged under flowing He (25 sccm) for 10 min. Samples were pretreated in situ at 200 °C with 10% $O_2$/He for 2 h, followed by reduction at 200 °C with 10% $H_2/N_2$ for 20 min, He purge at 200 °C for 10 min, then cooled to 40 °C for $NH_3$ or $CO_2$ or CO chemisorption. After the adsorption, samples were purged under flowing He (25 sccm) for 10 min, then the samples were heated up to 500 or 250 °C at a rate of 10 °C $min^{-1}$.

XRD patterns were recorded using a Philips X'pert MPD (Model PW3040/00) diffractometer with a copper anode (Ka1=0.15405 nm) and a scanning rate of 0.0013° per second between 2 h=10° and 90°. Jade 5 (Materials Data Inc., Livermore, CA) and the Powder Diffraction File database (International Center for Diffraction Data, Newtown Square, PA) were used to analyze the diffraction patterns.

The carbon, hydrogen, nitrogen, and sulfur composition of the $Pt/TiO_2$ catalyst before and after reaction was determined using a Thermo Fisher Flash 2000 CHNS/O organic elemental analyzer (Thermo Fisher Scientific, Inc., Waltham, MA). About 10 mg of sample was used for each analysis.

ICP (inductively coupled plasma) was used to quantify the amount of Pt present on the Pt/$TiO_2$ catalyst before and after reaction. ICP used a Perkin-Elmer 3000DV with an AS90 Autosampler, which has an instrument detection limit of ≈1 ppb. About 10 mg of solid sample was prepared via microwave digestion in concentrated acid and then diluted to volume.

Examples and Discussion

Figure 1:
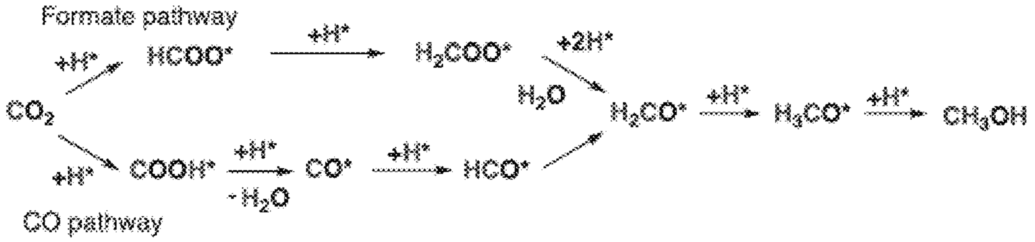
FIG. 1: Proposed gas phase (A) and condensed-phase (B) methanol synthesis from $CO_2$ and $H_2$.
Figure 1:
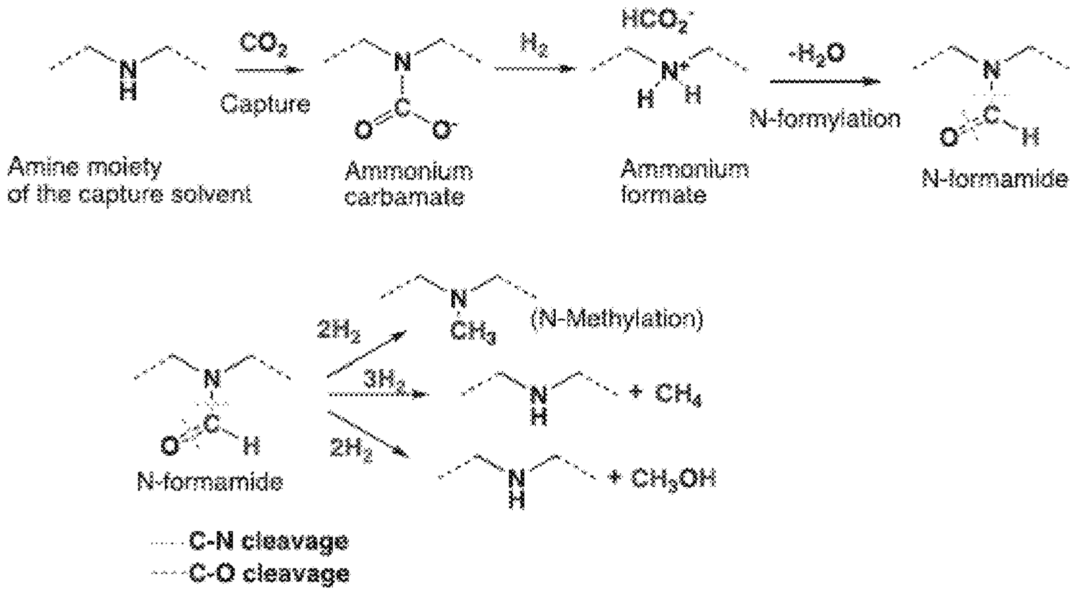
Figure 2:
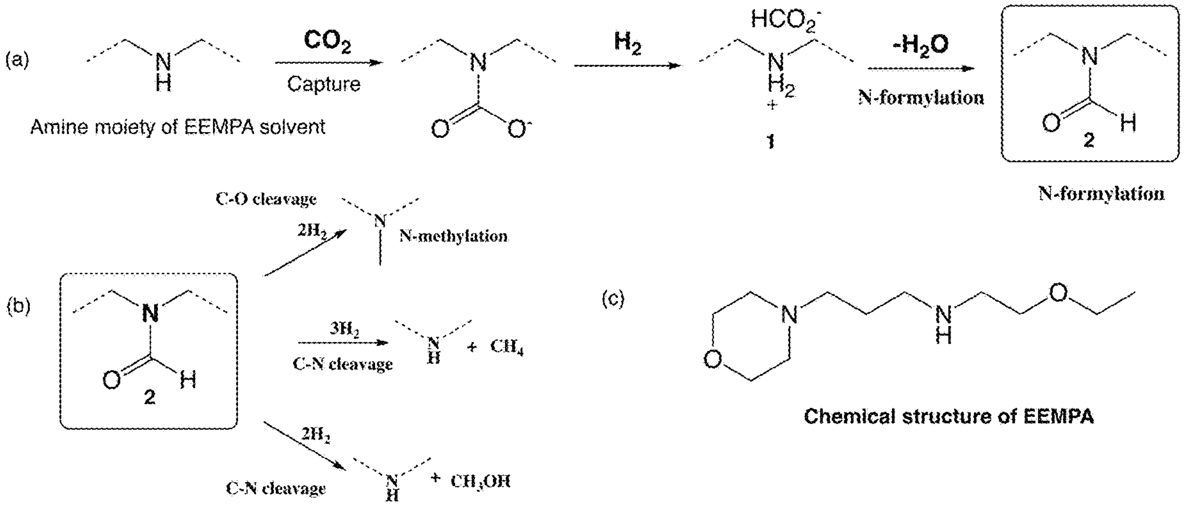
FIG. 2: Reaction mechanism of post-combustion solvent system.

The hydrogenation of captured $CO_2$ was studied using EEMPA as a water-lean post combustion capture solvent. First, the $CO_2$ captured in EEMPA solvent (10 wt % $CO_2$ loading) was subjected to hydrogenation in the presence of an industrial gas phase methanol catalyst, Cu/ZnO/$Al_2O_3$ (entry 1, table 1). The undesired N-methylation of EEMPA was observed as a major product by $^1H$ NMR. To confirm N-methylation, operando NMR was performed with $^{13}C$-enriched $CO_2$ (shown in FIG. 6). At 25 °C, under $^{13}CO_2$ and $H_2$ atmosphere, mostly the EEMPACOO-(carbamate) species was observed at 159.2 ppm in addition to $^{13}CO_2$ at 125.2 ppm. Upon heating this to 170 °C, the following new species were observed: $^{13}CO$, EEMPA+$H^{13}CO_2$— (formate), $H^{13}CO_2C_2H_5$ (ester), EEMPA-$^{13}CHO$ (formamide) and EEMPA-$^{13}CH_3$ (N-methylated EEMPA). The major species was the EEMPA-$^{13}CH_3$ (the $^{13}CH_3$ signal observed at 41.7 ppm), which was formed as a result of $^{13}CO_2$ acting as a N-methylating agent. Similar N-methylation of amines was reported in the literature with Cu/$Al_2O_3$ catalyst.[2] Literature reports have also shown that the rate of formation of N-methylated amine increased (and methanol decreased) at higher temperature, but the mechanism for the N-methylation is still not known.[3] It is also believed that the in situ (FIG. 1). The C—N cleavage is preferred as C—O cleavage results in deactivation of the capture solvent via N-methylation.

Under the experimental conditions shown in Table 1, entry 1, the C—N cleavage selectivity was ~25% in the case of Cu/ZnO/$Al_2O_3$. A CO formation was also observed via the reverse water gas shift reaction (RWGS) as a side product. The use of other amphoteric oxide supports such as hydrotalcite and $ZrO_2$ resulted in suppression of methanol product and only N-formamide and EEMPA-N-Me products were observed in addition to CO (Table 1, entries 2 and 4). A decreased $CO_2$ loading (5 wt %) improved the overall conversion and reduced RWGS reaction although the C—N cleavage selectivity remained mostly unchanged (Table 1, entry 1 vs 3). The acidic supports such as $CeO_2$ and $TiO_2$ completely suppressed both the methanol and EEMPA-Me formation, however the EEMPA-CHO was observed as a major product in both cases, which indicates that these supports in combination with Cu are not effective for the hydrogenation of the formamide intermediate under these reaction conditions (Table 1, entries 5 and 6). Overall, the surface acidity/basicity of the oxide supports considerably influenced the performance and selectivity of the catalyst (Table 1, entries 1-6).

Milstein et al. have shown that Ag/$Al_2O_3$ catalyst was effective for the selective C—N cleavage in the case of hydrogenation of benzamides and aliphatic amides under basic conditions.[4] Because formamide is an important intermediate observed under our reaction conditions, 30 wt % Ag/$Al_2O_3$ was screened for the hydrogenation of captured $CO_2$ to improve the C—N cleavage selectivity for the hydrogenation of in-situ formed formamide intermediate, EEMPA-CHO (Table 1, entry 7). Unfortunately, Ag/$Al_2O_3$ was very slow for the hydrogenation of EEMPA-CHO. In addition, there was no selectivity for C—N cleavage resulting in N-methylation of EEMPA.

TABLE 1

Hydrogenation of captured $CO_2$ in the presence of Cu and Ag catalysts using batch reactor system.

| Entry | Exp. No. | Catalyst | CO2 conv. (%) | Product selectivity (%) CO | $CH_4$ | EEMPA-CHO | EEMPA-Me | Methanol | Methanol Yield (%) | C—N cleavage selectivity (%) |
|---|---|---|---|---|---|---|---|---|---|---|
| 1[a] | 218 | 64 wt % Cu/ZaO/$Al_2O_3$ | 40.2 | 21.4 | 0.0 | 0.0 | 59.0 | 19.6 | 7.9 | 24.9 |
| 2[a] | 251 | Cu/ZaO/hydrotalcite | 34.2 | 16.3 | 4.7 | 15.7 | 63.3 | 0.0 | 0.0 | 0.0 |
| 3[b] | 283 | 64 wt % Cu/ZnO/$Al_2O_3$ | 62.3 | 14.2 | 0.0 | 0.0 | 65.8 | 20.0 | 12.5 | 23.3 |
| 4[b] | 263 | Cu/Za/$ZrO_2$ | 60.5 | 10.7 | 0.0 | 31.2 | 58.1 | 0.0 | 0.0 | 0.0 |
| 5[b] | 270 | 5 wt % Cu/$CeO_2$ | 3.4 | 0.0 | 0.0 | 100.0 | 0.0 | 0.0 | 0.0 | — |
| 6[b] | 281 | 35 wt % Cu/$TiO_2$ | 15.7 | 5.6 | 0.0 | 76.6 | 17.8 | 0.0 | 0.0 | 0.0 |
| 7[b] | 261 | 30 wt % Ag/$Al_2O_3$ | 30.6 | 0.0 | 1.0 | 72.8 | 26.3 | 0.0 | 0.0 | 0.0 |

Conditions: catalyst = 200 mg, 170° C., EEMPA-5 g ($CO_2$ loaded EEMPA used), initial P($H_2$) = 60 bar, time = 12 h,
[a]EEMPA-(10 wt %) $CO_2$,
[b]EEMPA-(6 wt %) $CO_2$, Cu/ZnO/$Al_2O_3$ = Cu (64 wt %)/ZnO(24 wt %)/$Al_2O_3$(5 wt %), formed methanol can act as a N-methylating agent. The fact that operando NMR studies only showed traces of methanol, but excess of EEMPA-$^{13}CHO$ species, it is likely the N-methylation occurs through the formamide intermediate. The formamide can undergo C—O cleavage to form N-methylated amine or C—N cleavage to form methanol Traditional gas-phase $CO_2$ hydrogenation catalysts deactivated the solvent via N-methylation of the 2° amine moiety.

Higher conversion demonstrated at lower $CO_2$ loading.

The methanol selectivity compared to EEMPA N-Me was <25% in all these cases.

TABLE 2

| Ethanol co-feed facilitates methanol production. | | | | | | | | |
|---|---|---|---|---|---|---|---|---|
| Entry | Capture Solvent | Exp. No. | $CO_2/H_2$ (bar) | Time (h) | Formamide (mmol) | N-methylamine (mmol) | $CH_3OH$ (mmol) | $CH_3OH$ Selectivity (%) |
| 1 | EEMPA | 62711-153 | 15/45 | 12 | 0.8 | 2 | 0.65 | 24.5 |
| 2 | EEMPA | 62711-148 | 15/45 | 48 | 0.45 | 5.1 | 1.23 | 19.4 |
| 3 | EEMPA | 62711-147 | 5/55 | 48 | 0.04 | 5.85 | 1.19 | 16.9 |
| 4[a] | EEMPA + ethanol | 62711-150 | 5/55 | 48 | traces | 1 | 2.4 | 70.6 |

Catalyst: $Cu/ZnO/Al_2O_3$ = 200 mg, 100 mL reactor, EEMPA = 23 mmol, P = 60 bar ($CO_2$:$3H_2$), T = 170° C., t = 12 h,
[a]ethanol = 200 mmol, only the liquid phase $CO_2$ derived products shown.

Ethanol co-feed facilitates reaction through formate ester intermediate, which was more selective to methanol than N-formamide intermediate.

With leading PNNL post-combustion system EEMPA, process conditions tailored to form methanol with 71% selectivity.

The formation of methanol in the presence of a post combustion solvent has, we believe, been demonstrated for the first time in the presence of a heterogenous catalyst.

Several different co-feeds and process conditions were evaluated with goal to improve methanol selectivity through N-formamide intermediate.

N-formamide is harder to reduce versus formate ester

Selectivity and conversion is higher if we form the ester species

Using ethanol would complicate the processing and add costs 5 wt % $Pd/Zn/Al_2O_3$ was screened for the hydrogenation of captured $CO_2$ (Table 3, entry 1). The selectivity and performance of the 5 wt % $Pd/ZnO/Al_2O_3$ was comparable to that of $Cu/ZnO/Al_2O_3$. Upon testing the roles of Al2O3 and ZnO with 5 wt % Pd separately, it was revealed that the combination of both $Al_2O_3$ and ZnO were required for higher $CO_2$ conversion (Table 3, entries 2 and 3). In particular, the C—N cleavage selectivity was further reduced with 5 wt % $Pd/Al_2O_3$ catalyst. The Pd on $Ga_2O_3$ support predominately formed methane and some amount of CO. No N-methylation was observed in this case. A lower $CO_2$ loading (Table 3, entry 5) showed no improvement in the $CO_2$ conversion unlike the $Cu/ZnO/Al_2O_3$ catalyst (in Table 1, entries 1 and 3) suggesting possibly different mechanistic pathways involved irrespective of similar product distributions with $Pd/Zn/Al_2O_3$ and $Cu/ZnO/Al_2O_3$ catalysts.

The Pd on an inert support, carbon, formed EEMPA-Me with good selectivity along with small amounts of CO and methane as side products (Table 1, entry 8). A basic support such as MgO significantly improved the C—N cleavage selectivity to ~55% (Table 1, entry 9) although the methanol yield was lower than the entry 1, Table 3 with 5wt % $Pd/ZnO/Al_2O_3$. Similar to the basic support, the Pd on an acidic support ($CeO_2$) also remarkably improved the C—N cleavage selectivity to ~70%, resulting in significant suppression of the N-methylation.

TABLE 3

| Hydrogenation of captured $CO_2$ in the presence of Pd catalysts using batch reactor system. | | | | | | | | | | |
|---|---|---|---|---|---|---|---|---|---|---|
| | | | CO2 | Product selectivity (%) | | | | | Methanol | C—N cleavage |
| Entry | Exp. No. | Catalyst | conv. (%) | CO | $CH_4$ | EEMPA-N—CHO | EEMPA N—Me | Methanol | Yield (%) | selectivity (%) |
| 1[a] | 172 | 5 wt % $Pd/ZnO/Al_2O_3$ | 54.3 | 14.3 | 0.2 | 22.9 | 52.0 | 10.4 | 5.7 | 16.7 |
| 2[a] | 255 | 5 wt % $Pd/Al_2O_3$ | 30.5 | 6.0 | 1.9 | 50.6 | 37.7 | 3.8 | 1.2 | 9.1 |
| 3[a] | 174 | 5 wt % Pd/ZnO | 20.7 | 38.7 | 0.0 | 5.3 | 42.8 | 13.2 | 2.7 | 23.5 |
| 4[a] | 249 | 5 wt % $Pd/Ga_2O_3$ | 9.3 | 14.0 | 86.0 | 0.0 | 0.0 | 0.0 | 0.0 | — |
| 5[b] | 254 | 5 wt % $Pd/Zn/Al_2O_3$ | 55.3 | 13.3 | 2.6 | 13.7 | 60.0 | 10.4 | 5.8 | 14.8 |
| 6[b] | 272 | 5 wt % Pd/hydrotalcite | 3.3 | 40.2 | 20.1 | 39.7 | 0.0 | 0.0 | 0.0 | — |
| 7[b] | 260 | 5 wt % $Pd/ZnO/Al_2O_3$ (reduced at 400° C.) | 39.8 | 14.4 | 1.1 | 9.9 | 64.5 | 10.1 | 4.0 | 13.5 |
| 8[b] | 269 | 5 wt % Pd/C | 18.5 | 4.4 | 2.4 | 0.0 | 93.2 | 0.0 | 0.0 | 0.0 |
| 9[b] | 271 | 5 wt % Pd/MgO | 13.3 | 8.3 | 5.5 | 57.2 | 13.2 | 15.8 | 2.1 | 54.5 |
| 10[b] | 266 | 5 wt % $Pd/CeO_2$ | 16.5 | 11.6 | 4.0 | 45.9 | 10.6 | 28.0 | 4.6 | 72.6 |
| 11[b,c] | 267 | 5 wt % $Pd/CeO_2$ | 25.4 | 5.8 | 1.3 | 59.9 | 10.3 | 22.7 | 5.8 | 68.8 |

[a]EEMPA-$CO_2$,
[b]EEMPA-$1/2CO_2$,
[c]ethanol, 5 wt % $Pd/ZnO/Al_2O_3$ = 200 mg, Pd/Zn ratio = 0.25

Figure 7A:
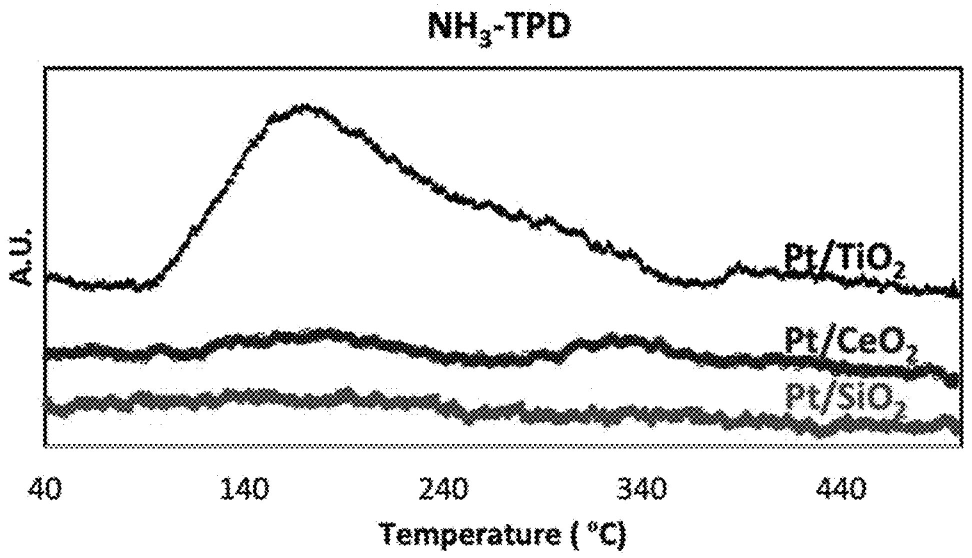
FIG. 7: $NH_3$-TPD (FIG. 7A) and $CO_2$-TPD (FIG. 7B). Conditions: Ammonia (10 mol % $NH_3$ in He) and $CO_2$ (10 mol % $CO_2$ in He) were adsorbed on 100 mg of sample. We loaded 100 mg of sample and purged under flowing He (25 sccm) for 10 min. Samples were pretreated in situ at 200 °C with 10% $O_2$/He for 2 h, followed by reduction at 200 °C with 10% $H_2/N_2$ for 20 min, He purge at 200 °C for 10 min, then cooled to 40 °C for NH3 or CO2 chemisorption. After the adsorption, samples were purged under flowing He (25 sccm) for 10 min, then the samples were heated up to 500 °C at a rate of 10 °C/min. Resulting $NH_3$ and $CO_2$ uptakes are presented in Table 4. (TPD=temperature programmed desorption)
Figure 7B:
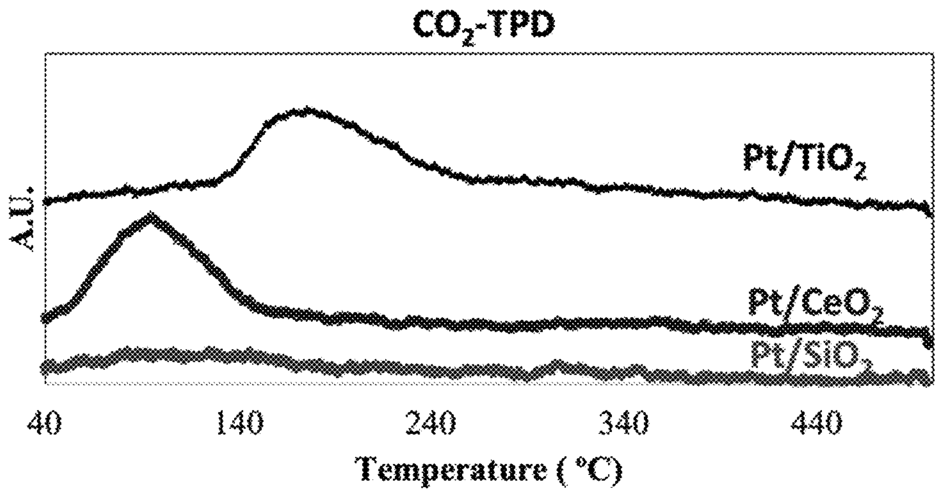

$Pt/CeO_2$ was screened under similar reaction conditions (Table 5, entry 1). Similar to $Pd/CeO_2$, $Pt/CeO_2$ formed methanol with high C—N bond cleavage selectivity. In addition, a considerable amount of CO was also formed in the gas phase by the rWGS reaction. The CO formation via decarbonylation of methanol has been reported in the literature.[21] The $TiO_2$ support behaved similar to $CeO_2$, albeit with more methane formation and less CO production (Table 5, entry 1 vs. 2). While no methanol was formed in the case of Pt on a $SiO_2$ support, more CO was formed relative to Pt on a $TiO_2$ support (Table 1, entry 2 vs. 3). In order to understand the role of the support on the reaction mechanism, we performed $CO_2$-TPD (TPD=temperature programmed desorption) and $NH_3$-TPD to evaluate the acidic and basic nature of the $Pt/TiO_2$, $Pt/SiO_2$ and $Pt/CeO_2$ catalysts (FIGS. 7A and 7B, Table 4). The TPD analyses showed that $Pt/TiO_2$ has both acidic and basic sites, while the $Pt/CeO_2$ catalyst contains mostly basic sites and the $Pt/SiO_2$ does not have acidic or basic sites. This suggests that the basicity offered by the $TiO_2$ and $CeO_2$ supports suppresses N-methylation (see FIG. 1). Based on the experimental and TPD results, a plausible reaction mechanism for the methanol, CO and $CH_4$ formation from the captured $CO_2$ has been shown in FIG. 9. First, the captured $CO_2$ (i.e, carbamate) coordinates to the catalyst surface, followed by hydrogenation with hydrogen activated by Pt to form a formate species, B. The in situ formed formate species, B, formylates the amine and forms an N-formamide intermediate, E. The nucleophilic attack of the lattice oxygen of the support on the carbonyl carbon of the N-formamide intermediate, E, and subsequent hydrogenation and deamination results in the formaldehyde intermediate, H, which then gets hydrogenated again to form methanol. We believe the participation of the lattice oxygen in the nucleophilic attack of the carbon of the N-formamide intermediate is the key to the C—N cleavage selectivity. Recent reports in the literature for alcoholysis of amides have indicated that both basic and acidic sites offered by $CeO_2$ surfaces are required for selective C—N cleavage. However, the mechanistic understanding on the synergistic effect between Pt and the acid-base pairs offered by the supports requires further investigation.

TABLE 4

Acidity and basicity of 5 wt % Pt catalysts using $NH_3$ and $CO_2$ TPD.

| Entry | Catalysts | Acidity $NH_3$-TPD (μmol/g) | Basicity $CO_2$-TPD (μmol/g) |
|---|---|---|---|
| 1 | 5 wt % $Pt/TiO_2$ | 24.4 | 5.6 |
| 2 | 5 wt % $Pt/CeO_2$ | 2.7 | 6.1 |
| 3 | 5 wt % $Pt/SiO_2$ | n.d | n.d |

100 mg of sample loaded and purged under flowing He (25 sccm) for 10 min. Samples were pretreated in situ at 200° C. with 10% $O_2$/He for 2 h, followed by reduction at 200° C. with 10% $H_2/N_2$ for 20 min, He purge at 200° C. for 10 min, then cooled to 40° C. for $NH_3$ or $CO_2$ chemisorption. After the adsorption, samples were purged under flowing He (25 sccm) for 10 min, then the samples were heated up to 500° C. at a rate of 10° C./min.

Because of the favorable chemical stability of $TiO_2$ in organic solvents, its strong metal-support interactions, and its acid-base properties, the $Pt/TiO_2$ system was explored further with different process conditions. The addition of ethanol as a co-solvent was also evaluated and improved the yields of the 2-EEMPA-CHO intermediate and methanol and decreased the yields of side products, CO, and methane (Table 5, entry 4). However, from the economic feasibility point of view, it is beneficial to avoid using ethanol as the co-solvent in the system. Because ethanol used for $CO_2$ conversion needs to be separated from the conversion products as well as from the carbon capture solvent, before recycling the carbon capture solvent to the $CO_2$ absorber. These separations are energy- and capital-intensive involving large distillation columns, big reboilers, and additional process units to break azeotropic between ethanol and water by-product. At low reaction temperatures (e.g., 150 °C) and with short reaction times, methanol was formed with high selectivity, and 100% selectivity toward C—N bond cleavage was observed (Table 5, entries 5 and 7). Table 5, entry 5 clearly shows that N-methylation and methanol formation do not occur in parallel with $Pt/TiO_2$-instead, the methanol is likely acting as an N-methylation source. Thus, by avoiding the longer contact time between the methanol and catalyst, N-methylation can be avoided. On the other hand, at lower $H_2$ pressure, the methanol yield and C—N bond cleavage selectivity were decreased (Table 5, entry 6). The commonly employed post-combustion solvent 30 wt % MEA was also evaluated for the hydrogenation of captured $CO_2$ with a $Pt/TiO_2$ catalyst (Table 5, entry 8). $^1$H NMR analysis revealed the formation of mostly MEA-formate, MEA-N-CHO species, and several MEA decomposition products (FIG. 8). This shows that the current approach of combined capture and conversion to methanol is not practical when using the conventional MEA solvent, in large part because the reaction involves elimination of water, and the formation of water is hindered in aqueous solution (FIG. 1).

TABLE 5

Hydrogenation of captured $CO_2$ in the presence of Pt-supported catalysts using batch reactor system.

| Entry | Catalyst | $CO_2$ conv. (%) | Product selectivity (%) CO | $CH_4$ | EEMPA-N—CHO | EEMPA N—Me | Methanol | Methanol Yield (%) | C—N cleavage selectivity (%) |
|---|---|---|---|---|---|---|---|---|---|
| 1 | 5 wt % $Pt/CeO_2$ | 29.7 | 49.5 | 3.3 | 11.4 | 11.4 | 24.4 | 7.2 | 68.0 |
| 2 | 5 wt % $Pt/TiO_2$ | 29.1 | 31.9 | 19.8 | 9.0 | 12.3 | 27.0 | 7.9 | 68.7 |
| 3 | 5 wt % $Pt/SiO_2$ | 23.9 | 77.4 | 0.0 | 15.3 | 7.3 | 0.0 | 0.0 | 0.0 |
| 4[a] | 5 wt % $Pt/TiO_2$ | 42.4 | 15.6 | 7.8 | 37.7 | 11.7 | 27.2 | 11.5 | 69.8 |
| 5[b] | 5 wt % $Pt/TiO_2$ | 11.5 | 35.8 | 25.6 | traces | traces | 38.7 | 4.5 | 100.0 |
| 6[d] | 5 wt % $Pt/TiO_2$ | 15.9 | 0.9 | 25.9 | 18.1 | 26.4 | 28.6 | 4.5 | 52.0 |
| 7[e] | 5 wt % $Pt/TiO_2$ | 12.2 | 25.5 | 22.4 | 15.0 | traces | 37.1 | 4.5 | 100.0 |

TABLE 5-continued

Hydrogenation of captured $CO_2$ in the presence of Pt-supported catalysts using batch reactor system.

| Entry | Catalyst | $CO_2$ conv. (%) | Product selectivity (%) CO | $CH_4$ | EEMPA-N—CHO | EEMPA N—Me | Methanol | Methanol Yield (%) | C—N cleavage selectivity (%) |
|---|---|---|---|---|---|---|---|---|---|
| 8[f] | 5 wt % $Pt/TiO_2$ | 44.7 | 5.8 | 1.6 | 38.1 | 5.9 | 7.6 | 3.4 | 56.5 |
| 9[c] | 5 wt % $Pt/TiO_2$ | 19.3 | 29.8 | 16.9 | 10.6 | 10.1 | 32.6 | 6.3 | 76.4 |

Conditions: catalyst = 200 mg, 170° C., EEMPA-5 g ($CO_2$ loaded EEMPA used, 6 wt % $CO_2$ loading), initial $P(H_2)$ = 60 bar, time = 12 h,
[a]ethanol,
[b]3 h,
[c]10 wt % $CO_2$,
[d]30 bar $H_2$,
[e]150° C.,
[f]30 wt % MEA was used as a capture solvent; mostly MEA-formate and MEA-N-formamide species were observed; MEA decomposition products were also observed under the reaction conditions.

Figure 6:
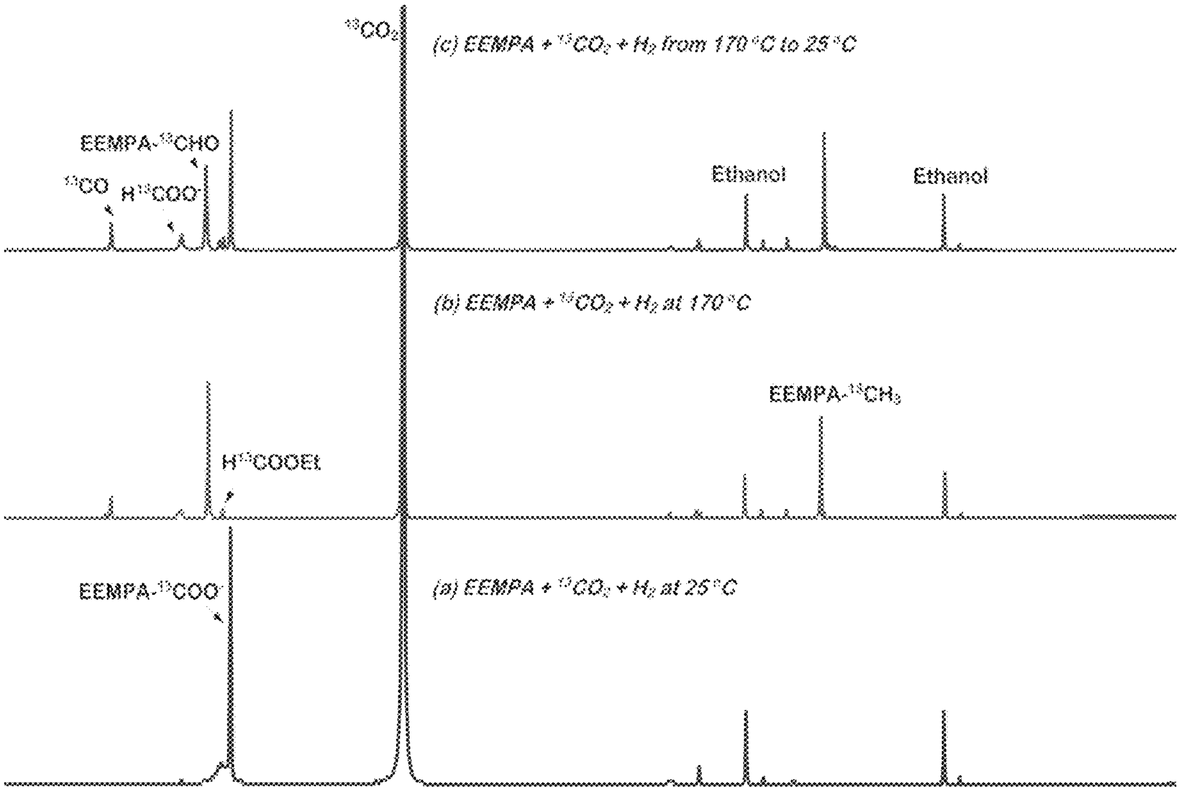
FIG. 6: In situ $^{13}C$ MAS-NMR during the hydrogenation of $^{13}CO_2$ in the presence of 2-EEMPA and the Cu/ZnO/$Al_2O_3$ catalyst at 170 °C under 60 bar $H_2$ (initial pressure) in ethanol co-solvent, 2-EEMPA:EtOH=1:10 (molar ratio).

In additional batch reactor studies, the $TiO_2$ support was screened with different metals such as Ni, Ru, Cu, and Pd to understand the role of Pt in selective C—N bond cleavage (Table 6). In the reactions with Ni and Ru, methane was formed with high selectivity and no methanol was observed (Table 6, entries 2 and 3). To the best of our knowledge, this is the first example of methane formation from captured $CO_2$ using a non-noble metal catalyst in the presence of a capture solvent. No methanol was observed in the presence of a $Cu/TiO_2$ catalyst, but only N-methylation was observed via 2-EEMPA-$^{13}$CHO, $^{13}CH_3OH$, and $^{13}CH_4$ as predominant species at 183.1, 164.4, 49.1, and −11 ppm, respectively, at 170 °C. Simultaneous formation of all these species suggests that methanol can form via both CO and N-formamide intermediates. CO could also form from the decarbonylation of methanol. It is very important to note that no detectable amount of the undesired 2-EEMPA-$^{13}CH_3$ species was observed, unlike the $Cu/ZnO/Al_2O_3$ catalyst under similar reaction conditions (FIG. 6 vs. FIG. 10).

TABLE 6

Hydrogenation of captured $CO_2$ in the presence of metals with $TiO_2$ supports using batch reactor system.

| Entry | Exp. No. | Catalyst | $CO_2$ conv. (%) | Product selectivity (%) CO | $CH_4$ | EEMPA-N—CHO | EEMPA N—Me | Methanol | $C_{2+}$ | Methanol Yield (%) | C—N cleavage selectivity (%) |
|---|---|---|---|---|---|---|---|---|---|---|---|
| 1 | 274 | 5 wt % $Pt/TiO_2$ | 29.1 | 31.9 | 19.8 | 9.0 | 12.3 | 27.0 | 0 | 7.9 | 68.7 |
| 2 | 287 | 35 wt % $Ni/TiO_2$ | 77.9 | 0.0 | 91.4 | 6.4 | 0.0 | 0.0 | 2.2 | 7.2 | 68.0 |
| 3 | 300 | 5 wt % $Ru/TiO_2$ | >99 | 0.0 | >90 | 0.0 | 0.0 | 0.0 | >10 | 0.0 | — |
| 4 | 281 | 35 wt % $Cu/TiO_2$ | 15.7 | 5.6 | 0.0 | 76.6 | 17.8 | 0.0 | 0.0 | 0.0 | 0.0 |
| 5 | 273 | 5 wt % $Pd/TiO_2$ | 19.9 | 3.7 | 16.2 | 80.1 | 0.0 | 0.0 | 0.0 | — | — |

Conditions: catalyst = 200 mg, 170° C., EEMPA-5 g ($CO_2$ loaded EEMPA used, 6 wt % $CO_2$ loading), initial $P(H_2)$ = 60 bar, time = 12 h undesired C—O bond cleavage (Table 5, entry 4, also shown in Table 1, entry 6). High Cu content on the $TiO_2$ support could have limited the availability of the $TiO_2$ support for the C—N cleavage selectivity. It is also important to note that low Cu content (5 wt %) in $Cu/CeO_2$ catalyst was not sufficient to hydrogenate the EEMPA-CHO intermediate (Table 1, entry 5).

When Pd was used in place of Pt, the $Pd/TiO_2$ was less active for the final formamide hydrogenation step (Table 3, entry 5) because Pd has a low concentration of hydrogen atoms on the surface compared to Pt.[24] Therefore, the results in Tables 5 and 6 clearly show that the combination of Pt and $TiO_2$ or $CeO_2$ supports is best suited for methanol production with reduced or negligible deactivation of the capture solvent.

Operando $^{13}$C NMR was performed with $^{13}$C-enriched $CO_2$ in the presence of a $Pt/TiO_2$ catalyst to understand the reaction pathway in the condensed phase and confirm the absence of N-methylation. The NMR analysis showed $^{13}$CO, The most promising catalyst formulation $Pt/TiO_2$ identified in batch reactor studies was then evaluated under continuous-flow operation for a range of operating temperatures and space velocities using $CO_2$ captured in neat 2-EEMPA solvent (Table 7). When operating at 140 °C, the $CO_2$ conversion was very low (2%) (Table 7, entry 1). However, the catalyst was highly selective toward methanol, with 93% selectivity. Interestingly, the remaining product was primarily propanol, with 7% selectivity. At higher temperatures (170 and 190 °C), ethanol and smaller amounts of butanol were also detected (Table 7, entries 2-8). While the mechanism for their formation is not yet clear, we can learn from decades of research on higher alcohol synthesis from the hydrogenation of CO and $CO_2$.[25,26] For example, the synergistic effects between metal nanoparticles and the underlying $TiO_2$ support, especially the anatase crystal phase with abundant oxygen vacancies, have been reported to facilitate ethanol formation from $CO_2$ and $H_2$.[27] Thus, this is a very important finding because the production of higher alcohols from syngas and/or $CO_2$ has been the subject of significant research in the area of conventional thermochemical catalysis. Furthermore, no CO or $CO_2$ was observed in the gas phase for any of the conditions evaluated. Confirmation that the reaction is primarily occurring in the condensed phase is significant, because any loss of carbon in the form of gas-phase CO or $CO_2$ would require additional energy and cost for recapture and conversion.

Also, when the operating temperature was increased from 140 to 190 °C (Table 7, entry 5), the $CO_2$ conversion modestly increased from 2% to 12%. However, the methanol selectivity was reduced from 93% to 78%. When higher alcohols were formed in addition to methanol, the generation of methane with 15% selectivity was also observed. While methane is considered an undesired side product in alcohol production reaction, the production of methane could have its advantages as a $CO_2$-neutral fuel. When operating at 190 °C, the space velocity was decreased by a factor of 10 and the conversion increased from 12% to 86% (Table 5, entries 4 and 6). However, methanol selectivity decreased from 78% to 52% because of increasing methane and ethane formation.

preferentially formed.[28] Physical changes to the catalyst (e.g., sintering/leaching of platinum particles) cannot be discarded, despite the mild conditions used. There was no appreciable change in the Pt dispersion between the fresh and spent catalysts based on the CO chemisorption (Table 8), suggesting no Pt sintering during the reaction. The presence of organic residue on the spent catalyst makes ICP (for Pt) and elemental analysis (C, H, N, S) quantification difficult or inconclusive. The Pt content of the fresh and spent $Pt/TiO_2$ catalysts was 5.6% and 4.5%, respectively. The capture solvent absorbed on the spent catalyst could be the reason for the low Pt content (and high C, H, N content) in the spent catalyst. The Pt crystallite size as determined by XRD remained below the detection limit. Further, XRD did not indicate any change in the $TiO_2$ support predominantly anatase phase after reaction. The XRD and elemental analysis (CHNSO) results are presented in FIG. 11.

TABLE 7

Hydrogenation of captured $CO_2$ over $Pt/TiO_2$ catalyst over a range of operating temperatures and space velocities using a continuous flow reactor system.

| Entry | Reaction temperature [° C.] | $CO_2$ Conversion [%] | WHSV $g_{CO2}/g_{cat}/h$ | TOS [h] | Selectivity [mol C %] MeOH | EtOH | PrOH | BuOH | $CH_4$ | $C_2H_6$ |
|---|---|---|---|---|---|---|---|---|---|---|
| 1 | 140 | 2.2 | 0.15 | — | 92.7 | 0.0 | 7.3 | 0.0 | 0.0 | 0.0 |
| 2 | 170 | 7.7 | 0.15 | — | 66.5 | 4.3 | 2.5 | 0.7 | 26.0 | 0.0 |
| 3 | 170 | 29.1 | 0.015 | — | 57.0 | 4.5 | 0.8 | 1.4 | 26.7 | 8.7 |
| 4 | 190 | 11.8 | 0.15 | — | 78.0 | 4.3 | 0.0 | 2.5 | 15.1 | 0.0 |
| 5 | 190 | 26.9 | 0.075 | — | 63.6 | 4.6 | 0.2 | 1.9 | 26.4 | 3.3 |
| 6 | 190 | 85.7 | 0.015 | 40 | 51.5 | 9.7 | 0.6 | 1.9 | 27.1 | 9.3 |
| 7 | 190 | 75.9 | 0.015 | 60 | 50.2 | 8.6 | 0.7 | 2.0 | 29.2 | 9.3 |
| 8 | 190 | 65.2 | 0.015 | 80 | 46.0 | 8.0 | 1.1 | 4.7 | 29.8 | 10.5 |

Liquid feed: captured $CO_2$ in EEMPA solvent (5 wt % $CO_2$) over 5 wt % $Pt/TiO_2$ catalyst. Reaction conditions: 1.0 g catalyst, 870 psig; Gas feed: (0.05, 0.025, 0.005 mL/min). 38 sccm $H_2$, 5 sccm $N_2$. Change in WHSV is achieved by changing the liquid feed flow. Catalyst was pretreated in situ overnight at 120° C. under reducing flow (50 sccm 10% $H_2$ in $N_2$).

Catalytic performance results in Table 7 (entries 6-8) show how the activity of $Pt/TiO_2$ decreases over time ($CO_2$ conversion steadily drops from 85.7% to 65.2% over 80 h of reaction). To understand possible underlying deactivation mechanisms, we performed postmortem characterization of the catalyst used in this reaction using diffuse reflectance infrared Fourier transform spectroscopy (DRIFTS), temperature-programmed oxidation with mass spectrometry (TPO-MS), X-ray powder diffraction (XRD), and inductively coupled plasma (ICP) and compared the results with those of the fresh catalyst. DRIFTS of the fresh and spent catalysts showed the presence of adsorbed water (FIG. 14). The spent catalyst also showed alkane C—H stretching bands between 3000 and 2800 $cm^{-1}$, which corresponds to the capture solvent (EEMPA). The main infrared features of the spent catalyst are the presence of CO adsorbed on Pt and of carbonate-like species in different adsorption modes (note that these carbonate-like species are also present in the fresh catalyst sample). The spent catalyst showed the presence of a terminal Pt—CO (2116 $cm^{-1}$) and a weak band at 1873 $cm^{-1}$ for bridged Pt—CO. Multiple bands appeared in the carbonate region between 1700 and 1200 $cm^{-1}$, corresponding to the carbonates, carbamates, and bicarbonates.[28] Both species (CO and carbonates) have been described in the literature as reasons for metal/support catalyst deactivation—in the case of CO due to a reduction of active sites on the Pt surface and in the case of carbonates due to a reduced number of interface Pt—$TiO_2$ active sites where they are

TABLE 8

Pt dispersion characterization of 5 wt % Pt catalysts using CO pulse chemisorption.

| Entry | Catalysts | CO Chemisorption Surface Pt (μmol/g) | CO Chemisorption Pt dispersion |
|---|---|---|---|
| 1 | 5 wt % $Pt/TiO_2$ | 72.5 | 28.6% |
| 2 | 5 wt % $Pt/TiO_2$ (spent) | 74.0 | 28.9% |
| 3 | 5 wt % $Pt/CeO_2$ | 63.4 | 25.1% |
| 4 | 5 wt % $Pt/SiO_2$ | 77.35 | 30.2% |

Analytical conditions: 100 mg of sample was purged under flowing He (25 sccm) for 10 min. Samples were pretreated in situ at 200° C. with 10% $O_2$/He for 2 h, followed by reduction at 200° C. with 10% $H_2/N_2$ for 20 min, He purge at 200° C. for 10 min, then cooled to 40° C. for CO chemisorption.

The TPO-MS analysis of the fresh $Pt/TiO_2$ catalyst showed signals for the loss of water between 150 and 500 °C (FIG. 15). The spent catalyst showed the presence of water, $CO_2$, and a small amount of CO. The metal-bound CO is possibly formed from the rWGS reaction. The following could be potential $CO_2$ sources: 1) the 2-EEMPA carbamate species bound to the Pt, which can release $CO_2$ with an increase in temperature (2-EEMPA-$CO_2$__ to 2-EEMPA+$CO_2$), 2) surface bicarbonate species formed upon the reaction of $CO_2$ or 2-EEMPA carbamate with water. The bicarbonate species can decompose to produce $CO_2$, water, and carbonate species ($2HCO_3$_ to $CO_2+H_2O+CO_3^{2-}$), 3) oxidation of adsorbed organic species such as $HCO_2^-$, 2-EEMPA, 2-EEMPA-CHO and 2-EEMPA-$CH_3$. The concurrent formation of water and $CO_2$ points to the oxidation of these organic species, 4) oxidation of adsorbed CO— under TPO conditions (10% $O_2$/He), the surface-bound CO species could oxidize to give $CO_2$ ($2CO+O_2$ to $2CO_2$). In addition, the TPO profile of the spent catalyst (FIG. 15) shows that desorption and oxidation of adsorbed species occur at moderate temperatures (<300 °C) and that CO gets desorbed at temperatures slightly higher than the reaction temperature (190 °C). This relatively strong (and extended) CO adsorption is consistent with literature reports, which indicate this as the main reason for Pt deactivation at these mild reaction temperatures (<200 °C) and for weaker CO—Pt adsorption at higher temperatures.[28] Solvent adsorbed on the catalyst (3000-2800 $cm^{-1}$ infrared bands in FIG. 14) decomposes also at moderate oxidation temperatures (NO peak max at 290 °C in FIG. 15). Both DRIFTS and TPO-MS analyses suggest that CO and carbonates are blocking the active sites of the spent catalyst. However, operando $^{13}C$ MAS-NMR showed only the presence of metal-bound CO under the reaction conditions (at 170 °C) and that the carbonate/carbamate/bicarbonate species are formed only at room temperature (FIG. 15). CO-TPD was performed on the CO chemisorbed $Pt/TiO_2$ catalyst to further evaluate strong CO adsorption. CO-TPD results suggest that CO is strongly bound to the catalyst surface (CO—Pt) even at the reaction temperature of 190 °C (FIG. 12). Overall, based on DRIFTS, in situ $^{13}C$ MAS-NMR, and TPO-MS, we conclude that the catalyst is most likely poisoned by the strong adsorption of CO on Pt. Regeneration/reactivation is possible at relatively moderate oxidation/desorption temperatures.

References

[1] https://www.un.org/en/climatechange/net-zero-coalition (accessed: September 2022).

[2] a) A. Al-Mamoori, A. Krishnamurthy, A. A. Rownaghi, F. Rezaci, *Energy Technol.* 2017, 5, 834; b) P. Gabrielli, M. Gazzani, M. Mazzotti, *Ind. Eng. Chem. Res.* 2020, 59, 7033; c) J. Leclaire, D. J. Heldebrant, *Green Chem.* 2018, 20, 5058; d) E. C. Ra, K. Y. Kim, E. H. Kim, H. Lee, K. An, J. S. Lec, *ACS Catal.* 2020, 10, 11318; c) M. Bui, C. S. Adjiman, A. Bardow, E. J. Anthony, A. Boston, S. Brown, P. S. Fennell, S. Fuss, A. Galindo, L. A. Hackett, J. P. Hallett, H. J. Herzog, G. Jackson, J. Kemper, S. Krevor, G. C. Maitland, M. Matuszewski, I. S. Metcalfe, C. Petit, G. Puxty, J. Reimer, D. M. Reiner, E. S. Rubin, S. A. Scott, N. Shah, B. Smit, J. P. M. Trusler, P. Webley, J. Wilcox, N. M. Dowell, *Energy Environ. Sci.* 2018, 11, 1062; f) C. Hepburn, E. Adlen, J. Beddington, E. A. Carter, S. Fuss, N. M. Dowell, J. C. Minx, P. Smith, C. K. Williams, *Nature* 2019, 575, 87; g) J. Tollefson, *Nature* 2022, https://doi.org/10.1038/d41586-022-00585-7; h) M. Peplow, *Nature* 2022, 603, 780.

[3] National Academies of Sciences, Engineering, and Medicine, *Negative Emissions Technologies and Reliable Sequestration: A Research Agenda*, The National Academies Press, Washington DC 2019.

[4] https://www.iea.org/commentaries/is-carbon-capture-too-expensive (accessed: September 2022).

[5] X. Wang, C. Song, *Front. Energy Res.* 2020, 8, 560849.

[6] https://www.iea.org/reports/ccus-in-clean-energy-transitions (accessed: September 2022).

[7] D. W. Keith, G. Holmes, D. St. Angelo, K. Heidel, *Joule* 2018, 2, 1573.

[8] a) D. Aaron, C. Tsouris, *Sep. Sci. Technol.* 2005, 40, 321; b) P. Luis, *Desalination* 2016, 380, 93; c) D. J. Heldebrant, P. K. Koech, V. A. Glezakou, R. Rousseau, D. Malhotra, D. C. Cantu, *Chem. Rev.* 2017, 117, 9594; d) D. J. Heldebrant, J. Kothandaraman, in *Carbon Capture and Storage* (Eds: M. Bui, N. M. Dowell), The Royal Society of Chemistry, London 2020, p. 36-68.

[9] a) D. B. Lao, B. R. Galan, J. C. Linchan, D. J. Heldebrant, *Green Chem.* 2016, 18, 4871; b) J. Kothandaraman, R. A. Dagle, V. L. Dagle, S. D. Davidson, E. D. Walter, S. D. Burton, D. W. Hoyt, D. J. Heldebrant, *Catal. Sci. Technol.* 2018, 8, 5098; c) S. Xic, W. Zhang, X. Lan, H. Lin, *ChemSusChem* 2020, 13, 6141; d) S. Kar, A. Goeppert, G. K. S. Prakash, *Acc. Chem. Res.* 2019, 52, 2892; c) N. M. Rezaycc, C. A. Huff, M. S. Sanford, *J. Am. Chem. Soc.* 2015, 137, 1028; f) J. Kothandaraman, D. J. Heldebrant, *Green Chem.* 2020, 22, 828; g) M. Scott, B. Blas Molinos, C. Westhues, G. Francio, W. Leitner, *ChemSusChem* 2017, 10, 1085; h) J. Kothandaraman, J. Zhang, V.-A. Glezakou, M. T. Mock, D. J. Heldebrant, *J. CO2* Util. 2019, 32, 196; i) J. W. Maina, J. M. Pringle, J. M. Razal, S. Nunes, L. Vega, F. Gallucci, L. F. Dumec, *ChemSusChem* 2021, 14, 1805; j) J. B. Jakobsen, M. H. Ronne, K. Daasbjerg. T. Skrydstrup, *Angew. Chem., Int. Ed.* 2021, 60, 9174; k) J. Bi, P. Hou, F. W. Liu, P. Kang. *ChemSusChem* 2019, 12, 2195; l) M. Yadav, J. C. Linchan, A. J. Karkamkar, E. van der Eide, D. J. Heldebrant, *Inorg. Chem.* 2014, 53. 9849; m) R. Sen, C. J. Koch, A. Goeppert, G. K. S. Prakash, *Chem-Sus-Chem* 2020, 13, 6318; n) E. A. K. Wilson, S. C. Eady, T. Silbaugh, L. T. Thompson, M. A. Barteau, *J. Catal.* 2021, 404. 977; o) S. Ni, J. Zhu, R. Roy, C.-J. Li, R. B. Lennox, *Green Chem.* 2021, 23, 3740; p) M. Lu, J. Zhang, Y. Yao, J. Sun, Y. Wang, H. Lin, *Green Chem.* 2018, 20, 4292; q) J. R. Khusnutdinova, J. A. Garg. D. Milstein, *ACS Catal.* 2015, 5, 2416; r) N. D. McNamara, J. C. Hicks, *ChemSusChem* 2014, 7, 1114; s) C. Reller, M. Poge, A. Lissner, F. O. Mertens, *Environ. Sci. Technol.* 2014, 48, 14799; t) S. Overa, T. G. Feric, A.-H. A. Park, F. Jiao, *Joule* 2021, 5, 8; u) R. Sen, C. J. Koch, V. Galvan, N. Entesari, A. Goeppert, G. K. S. Prakash, *J. CO2 Util.* 2021, 54, 101762; v) D. Wei, H. Junge, M. Beller, *Chem. Sci.* 2021, 12, 6020; w) D. Wei, R. Sang, A. Moazezbarabadi, H. Junge, M. Beller, *JACS Au* 2022, 2, 1020; x) S. Kar, A. Goeppert, J. Kothandaraman, G. K. S. Prakash, *ACS Catal.* 2017, 7, 6347.

[10] a) M. Scott, C. G. Westhues, T. Kaiser, J. C. Baums, A. Jupke, G. Francio, W. Leitner, *Green Chem.* 2019. 21. 6307; b) J. Kothandaraman, D. J. Heldebrant, *RSC Adv.* 2021. 10, 42557; c) A. Sternberg, C. M. Jens, A. Bardow, *Green Chem.* 2017, 19, 2244; d) J. Klankermayer, W. Leitner, *Science* 2015, 350, 629; c) Q. Liu, L. Wu, R. Jackstell, M. Beller, *Nat. Commun.* 2015, 6, 5933; f) T. Sakakura, J. C. Choi, H. Yasuda, *Chem. Rev.* 2007, 107, 2365; g) G. A. Olah, A. Goeppert, G. K. Prakash, *J. Org. Chem.* 2009, 74, 487; h) J. Klankermayer, S. Wesselbaum, K. Beydoun, W. Leitner, *Angew. Chem., Int. Ed.* 2016, 55, 7296; i) C. Song, *Catal. Today* 2006, 115, 137. j) G. A. Olah, G. K. Prakash, A. Goeppert, *J. Am. Chem. Soc.* 2011, 133, 12881; k) S. van Bavel, S. Verma, E. Negro, M. Bracht, *ACS Energy Lett.* 2020, 5, 2597; l) Z. Zhang. T. Wang. M. J. Blunt, E. J. Anthony, A.-H. A. Park, R. W. Hughes, P. A. Webley, J. Yan, *Appl. Energy* 2020, 278, 115627.

[11] a) J. Kothandaraman, J. Saavedra Lopez, Y. Jiang, E. D. Walter, S. D. Burton, R. A. Dagle, D. J. Heldebrant, *ChemSusChem* 2021, 14, 4812; b) D. J. Heldebrant, J. Kothandaraman, N. M. Dowell, L. Brickett, *Chem. Sci.* 2022, 13, 6445.

[12] J. Kothandaraman, A. Goeppert, M. Czaun, G. A. Olah, G. K. Prakash, *J. Am. Chem. Soc.* 2016. 138, 778.

[13] a) S. Kanuri, S. Roy, C. Chakraborty, S. P. Datta, S. A. Singh, S. Dinda, *Int. J. Energy Res.* 2022, 46, 5503; b) M. D. Porosoff, B. Yan, J. G. Chen, *Energy Environ. Sci.* 2016, 9, 62; c) S. Kattel, P. J. Ramirez, J. G. Chen, J. A. Rodriguez, P. Liu, *Science* 2017, 355, 1296.

[14] a) S. Kar, J. Kothandaraman, A. Goeppert, G. K. S. Prakash, *J. CO2 Util.* 2018, 23, 212; b) S. Kar, R. Sen, J. Kothandaraman, A. Goeppert, R. Chowdhury, S. B. Munoz, R. Haiges, G. K. S. Prakash, *J. Am. Chem. Soc.* 2019, 141. 3160.

[15] Y. Jiang, P. M. Mathias, C. J. Freeman, J. A. Swisher, R. F. Zheng, G. A. Whyatt, D. J. Heldebrant, *Int. J. Greenhouse Gas Control* 2021. 106, 103279.

[16] a) R. F. Zheng. D. Barpaga, P. M. Mathias, D. Malhotra, P. K. Kocch, Y. Jiang, M. Bhakta, M. Lail, A. V. Rayer, G. A. Whyatt, C. J. Freeman, A. J. Zwoster, K. K. Weitz, D. J. Heldebrant, *Energy Environ. Sci.* 2020, 13, 4106; b) D. Malhotra, D. C. Cantu, P. K. Kocch, D. J. Heldebrant, A. Karkamkar, F. Zheng, M. D. Bearden, R. Rousseau, V.-A. Glezakou, *ACS Sustainable Chem. Eng.* 2019, 7, 7535; c) D. C. Cantu, D. Malhotra, M. T. Nguyen, P. K. Koech, D. Zhang, V. A. Glezakou, R. Rousseau, J. Page, R. Zheng, R. J. Perry, D. J. Heldebrant, *ChemSusChem* 2020, 13, 3429.

[17] S. V. Gredig, R. A. Koeppel, A. Baiker, *J. Chem. Soc., Chem. Commun.* 1995, https://doi.org/10.1039/c3995000007373.

[18] a) S. V. Gredig, R. Koeppel, A. Baiker, *Appl. Catal., A* 1997, 162, 249; b) S. V. Gredig, R. Koppel, A. Baiker, *Catal. Today* 1996, 29, 339; c) S. Auer, *J. Mol. Catal. A: Chem.* 1999, 14, 193.

[19] Y. Xic, P. Hu, T. Bendikov, D. Milstein, *Catal. Sci. Technol.* 2018, 8, 2784.

[20] M. K. Gnanamani, R. Garcia, G. Jacobs, K. Gora-Marek, D. C. Cronauer, A. J. Kropf, C. L. Marshall, *Appl. Catal., A* 2020, 602, 117722. a) A. Kaithal, B. Chatterjee, C. Werle, W. Leitner, *Angew. Chem., Int. Ed.* 2021, 60, 26500; b) W.-J. Shen Yasuyuki Matsumura, *Phys. Chem. Chem. Phys.* 2000, 2, 1519; c) Y. Liu, T. Hayakawa, T. Ishii, M. Kumagai, H. Yasuda, K. Suzuki, S. Hamakawa, K. Murata, *Appl. Catal., A* 2001, 210, 301; d) J. C. Brown, E. Gulari, *Catal. Commun.* 2004, 5, 431; c) S. A. Ranaweera, W. P. Henry, M. G. White, *ACS Omega* 2017, 2, 5949; f) G. Li, C. Gu, W. Zhu, X. Wang, X. Yuan, Z. Cui, H. Wang, Z. Gao, *J. Cleaner Prod.* 2018, 183, 415.

[22] T. Toyao, M. Nurnobi Rashed, Y. Morita, T. Kamachi, S. M. A. Hakim Siddiki, M. A. Ali, A. S. Touchy, K. Kon, Z. Maeno, K. Yoshizawa, K. i. Shimizu, *ChemCatChem* 2018, 11, 449.

[23] S. Bagheri, N. Muhd Julkapli, S. Bee Abd Hamid, *Sci. World J.* 2014, 2014, 727496.

[24] A. K. Talukdar, K. G. Bhattacharyya, S. Sivasanker, *Appl. Catal., A* 1993, 96, 229.

[25] J. J. Spivey, A. Egbebi, *Chem. Soc. Rev.* 2007, 36, 1514.

[26] a) V. Subramani, S. K. Gangwal, *Energy Fuels* 2008, 22, 814; b) D. Xu, Y. Q. Wang, M. Y. Ding, X. L. Hong, G. L. Liu, S. C. E. Tsang, *Chem* 2021, 7, 849.

[27] D. Wang, Q. Y. Bi, G. H. Yin, W. L. Zhao, F. Q. Huang, X. M. Xie, M. H. Jiang, *Chem. Commun.* 2016, 52, 14226.

[28] K. He, Q. Wang, *Catalysts* 2021, 11, 1280.

[29] a) J. Liu, F. R. Lucci, M. Yang, S. Lee, M. D. Marcinkowski, A. J. Therrien, C. T. Williams, E. C. Sykes, M. Flytzani-Stephan opoulos, *J. Am. Chem. Soc.* 2016, 138, 6396; b) A. I. Boronin, E. M. Slavinskaya, A. Figueroba, A. I. Stadnichenko, T. Y. Kardash, O. A. Stonkus, E. A. Fedorova, V. V. Muravev, V. A. Svetlichnyi, A. Bruix, K. M. Neyman, *Appl. Catal., B* 2021, 286, 119931; c) M. D. Argyle, C. H. Bartholomew, *Catalysts* 2015, 5, 145.

[30] L. Li, S. Miyazaki, S. Yasumura, K. W. Ting, T. Toyao, Z. Maeno, K.-i. Shimizu, *ACS Catal.* 2022, 12, 2639.

[31] A. Rödl, C. Wulf, M. Kaltschmitt, in *Hydrogen Supply Chains*, Academic Press, San Diego, CA 2018, p. 81-109.

[32] R. E. James, D. Kearins, M. Turner, M. Woods, N. Kuehn, A. Zoelle, NETL, *Cost and Performance Baseline for Fossil Energy Plants*, Vol. 1, Bituminous Coal and Natural Gas to Electricity 2019.

[33] Methanol production capacity may quintuple on decarbonized industry transformation: Study, https://cleanenergynews.ihsmarkit.com/research-analysis (accessed: September 2022).

[34] https://www.parrinst.com/products/stirred-reactors/series-4560-100-600-ml-mini-reactors/ (accessed: September 2022).

[35] E. D. Walter, L. Qi, A. Chamas, H. S. Mehta, J. A. Sears, S. L. Scott, D. W. Hoyt, *J. Phys. Chem. C* 2018, 122, 8209.

What is claimed:

1. A method of converting $CO_2$ to methanol comprising:

contacting a solution comprising $CO_2$ in an amine sorbent over a solid catalyst comprising a noble metal on a reducible metal oxide support at a temperature in the range of 181 °C to 225 °C;

wherein the $CO_2$ is post or pre combustion $CO_2$; and wherein the conversion of $CO_2$ occurs in a condensed phase and the $CO_2$ is converted to methanol with at least 40% selectivity; wherein the single pass conversion of $CO_2$ is at least 75%; and wherein the $C_{2+}$ alcohol selectivity, or the ethanol selectivity, is at least 4 mol %.

2. The method of claim 1 further comprising one or any combination of the following: wherein the methanol selectivity is at least 50 mol %; wherein the methanol selectivity is in the range of 40 to about 80 mol %; wherein the single pass conversion of $CO_2$ is in the range of 75 to about 90%; wherein the selectivity to ethanol is 4 to 10 mol %; wherein the selectivity to butanol is at least 1.7 mol %; wherein the selectivity to butanol is about 2 to about 5 mol %.

3. The method of claim 1 wherein the conversion of $CO_2$ is in a continuous flow operation.

4. The method of claim 1 occurring in a single pass.

5. The method of claim 1 comprising a single pass $CO_2$ conversion of 80-90%.

6. The method of claim 1 in which the catalyst support comprises $CeO_2$ or $TiO_2$.

7. The method of claim 1 in which the amine sorbent is a water-lean solvent.

8. The method of claim 1 further comprising separation and conversion of $CO_2$ from landfill gases, waste-water treatment gases, manure off-gas, fermenters, cement plants, steel kilns, and pulp and paper mills.

9. The method of claim 1 in which the amine sorbent is N-(2-ethoxyethyl)-3-morpholinopropan-1-amine(2-EE-MPA).

10. The method of claim 1 in which the amine sorbent comprises 0.5-20wt % $CO_2$ loading.

11. The method of claim 1 in which ethanol is a co-solvent.

12. The method of claim 1 in which CO and N-formamide are formed as intermediates.

13. A method of converting $CO_2$ comprising:

providing continuous flow reactor system comprising:

an absorber;

a pump; and a reactor;

enriching an amine sorbent with $CO_2$ by contacting the solvent with a flue gas comprising $CO_2$ to create a $CO_2$-enriched solution in the absorber;

pressurizing the $CO_2$-enriched solution to between 30 and 100 bar $H_2$;

heating the $CO_2$-enriched solution;

producing a heated and pressurized $CO_2$-enriched solution;

feeding the heated and pressurized $CO_2$-enriched solution with pressurized $H_2$ gas into a reactor comprising a solid catalyst comprising a noble metal on a reducible metal oxide support and reacting the solution over the solid catalyst at a temperature of between 181 and 225°C; and producing a product solution in which the $CO_2$ in the solution is converted into methanol, $C_{2+}$ alcohols, $CH_4$, and light hydrocarbons over the solid catalyst.

14. The method of claim 13 comprising a single pass $CO_2$ conversion of 80-90%.

15. The method of claim 14 in which the conversion of $CO_2$ occurs in a condensed phase.

16. The method of claim 13 wherein the solid catalyst comprises Pt disposed on a reducible metal oxide support.

17. The method of claim 16 wherein the catalyst support comprises $CeO_2$ and/or $TiO_2$.

18. The method of claim 13 wherein the amine sorbent is a water-lean post-combustion solvent.

19. A composition of matter comprising an amine solvent, $CO_2$, a heterogeneous catalyst comprising a noble metal disposed on a reducible metal oxide support, and methanol derived from the carbon dioxide, wherein the methanol derived from the $CO_2$ makes up at least 1% by mass of the $CO_2$ and wherein the molar ratio of the methanol produced from $CO_2$ to ethyl formate in the composition is greater than 2.

20. The composition of claim 19 in which the catalyst suppresses N- methylation of the amine solvent.

* * * * *